United States Patent
Bonner et al.

(10) Patent No.: US 7,493,154 B2
(45) Date of Patent: Feb. 17, 2009

(54) METHODS AND APPARATUS FOR LOCATING BODY VESSELS AND OCCLUSIONS IN BODY VESSELS

(75) Inventors: Matthew D. Bonner, Plymouth, MN (US); Cynthia T. Clague, Minnetonka, MN (US); Scott E. Jahns, Hudson, WI (US); James R. Keogh, Maplewood, MN (US)

(73) Assignee: Medtronic, Inc., Minneapolis, MN (US)

( * ) Notice: Subject to any disclaimer, the term of this patent is extended or adjusted under 35 U.S.C. 154(b) by 435 days.

(21) Appl. No.: 10/278,531

(22) Filed: Oct. 23, 2002

(65) Prior Publication Data
US 2004/0082850 A1    Apr. 29, 2004

(51) Int. Cl.
*A61B 5/05*    (2006.01)
(52) U.S. Cl. .................. 600/424; 600/585; 600/13; 604/164.13; 604/526
(58) Field of Classification Search ................ 600/424, 600/101, 114, 117, 129, 585, 13; 604/164.13, 604/525; 606/130
See application file for complete search history.

(56) References Cited

U.S. PATENT DOCUMENTS

| | | | | |
|---|---|---|---|---|
| 4,562,838 A | * | 1/1986 | Walker ...................... | 606/42 |
| 5,385,606 A | | 1/1995 | Kowanko .................... | 106/124 |
| 5,386,828 A | * | 2/1995 | Owens et al. ............... | 600/585 |
| 5,452,733 A | | 9/1995 | Sterman et al. ............. | 128/898 |
| 5,464,447 A | | 11/1995 | Fogarty et al. .............. | 607/129 |
| 5,695,504 A | | 12/1997 | Gifford, III et al. ......... | 606/153 |
| 5,707,380 A | | 1/1998 | Hinchiffe et al. ............ | 606/153 |
| 5,716,392 A | | 2/1998 | Bourgeois et al. ........... | 607/132 |
| 5,722,426 A | | 3/1998 | Kolff ......................... | 128/898 |
| 5,799,661 A | | 9/1998 | Boyd et al. ................. | 128/898 |
| 5,833,605 A | * | 11/1998 | Shah .......................... | 600/393 |
| 5,860,951 A | * | 1/1999 | Eggers et al. ............... | 604/510 |
| 5,868,770 A | | 2/1999 | Rygaard ..................... | 606/167 |
| 5,893,369 A | | 4/1999 | LeMole ...................... | 606/184 |
| 5,944,023 A | * | 8/1999 | Johnson et al. ............. | 128/899 |
| 5,972,017 A | | 10/1999 | Berg et al. .................. | 606/198 |
| 5,976,178 A | | 11/1999 | Goldsteen et al. ............ | 623/1 |
| 6,026,814 A | | 2/2000 | LaFontaine et al. ......... | 128/898 |
| 6,033,401 A | * | 3/2000 | Edwards et al. ............. | 606/41 |
| 6,061,588 A | * | 5/2000 | Thornton et al. ............ | 600/424 |
| 6,071,295 A | | 6/2000 | Takahashi ................... | 606/191 |
| 6,074,401 A | * | 6/2000 | Gardiner et al. ............ | 606/139 |

(Continued)

*Primary Examiner*—Brian L. Casler
*Assistant Examiner*—Baisakhi Roy
(74) *Attorney, Agent, or Firm*—Mike Jaro; Jeffrey J. Hohenshell

(57) ABSTRACT

Methods and apparatus employed to locate body vessels and occlusions in body vessels finding particular utility in cardiac surgery, particularly minimally invasive cardiac surgery to locate cardiac arteries and occlusions in cardiac arteries are disclosed. An elongated vessel lumen probe incorporating a lumen probe element at or near the elongated vessel lumen probe distal end is advanced into the vessel lumen. A vessel surface probe manipulated by the surgeon and having a surface probe element sensor is employed to detect the lumen probe element and to follow the progress of the vessel lumen probe element as it approaches and is advanced through or is blocked by an occlusion. In the location of a coronary artery, the surface probe element sensor is moved about against the epicardium over the suspected location of the artery of interest until a surface probe element sensor of the present invention at the surface probe distal end interacts with the lumen probe element of the vessel lumen probe.

57 Claims, 13 Drawing Sheets

U.S. PATENT DOCUMENTS

| | | | |
|---|---|---|---|
| 6,080,175 A | 6/2000 | Hogendijk | 606/185 |
| 6,113,588 A | 9/2000 | Duhaylongsod et al. | 606/15 |
| 6,213,126 B1 * | 4/2001 | LaFontaine et al. | 128/898 |
| 6,231,565 B1 | 5/2001 | Tovey et al. | 606/1 |
| 6,241,667 B1 | 6/2001 | Vetter et al. | 600/407 |
| 6,248,072 B1 | 6/2001 | Murkin | 600/446 |
| 6,248,117 B1 | 6/2001 | Blatter | 606/153 |
| 6,304,769 B1 * | 10/2001 | Arenson et al. | 600/424 |
| 6,332,468 B1 | 12/2001 | Benetti | 128/898 |
| 6,552,796 B2 * | 4/2003 | Magnin et al. | 356/450 |
| 6,579,311 B1 * | 6/2003 | Makower | 623/1.23 |
| 6,699,245 B2 * | 3/2004 | Dinger et al. | 606/49 |
| 6,869,437 B1 * | 3/2005 | Hausen et al. | 606/153 |

* cited by examiner

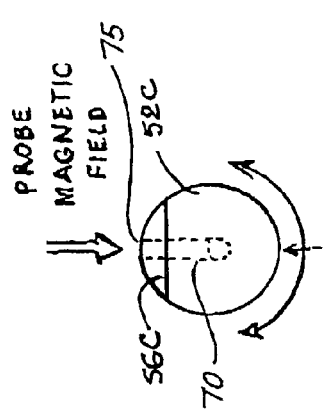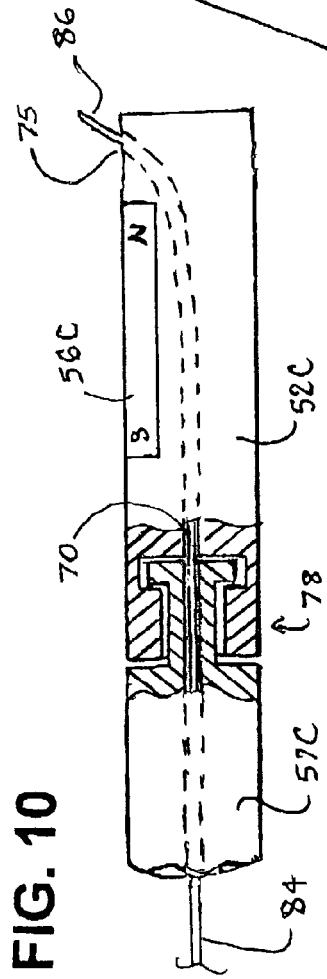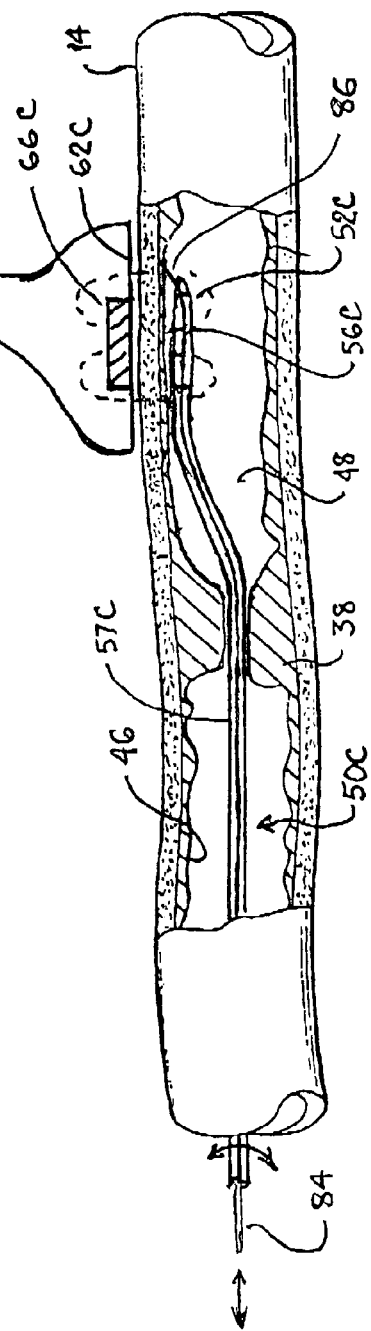
FIG. 9
FIG. 11
FIG. 10

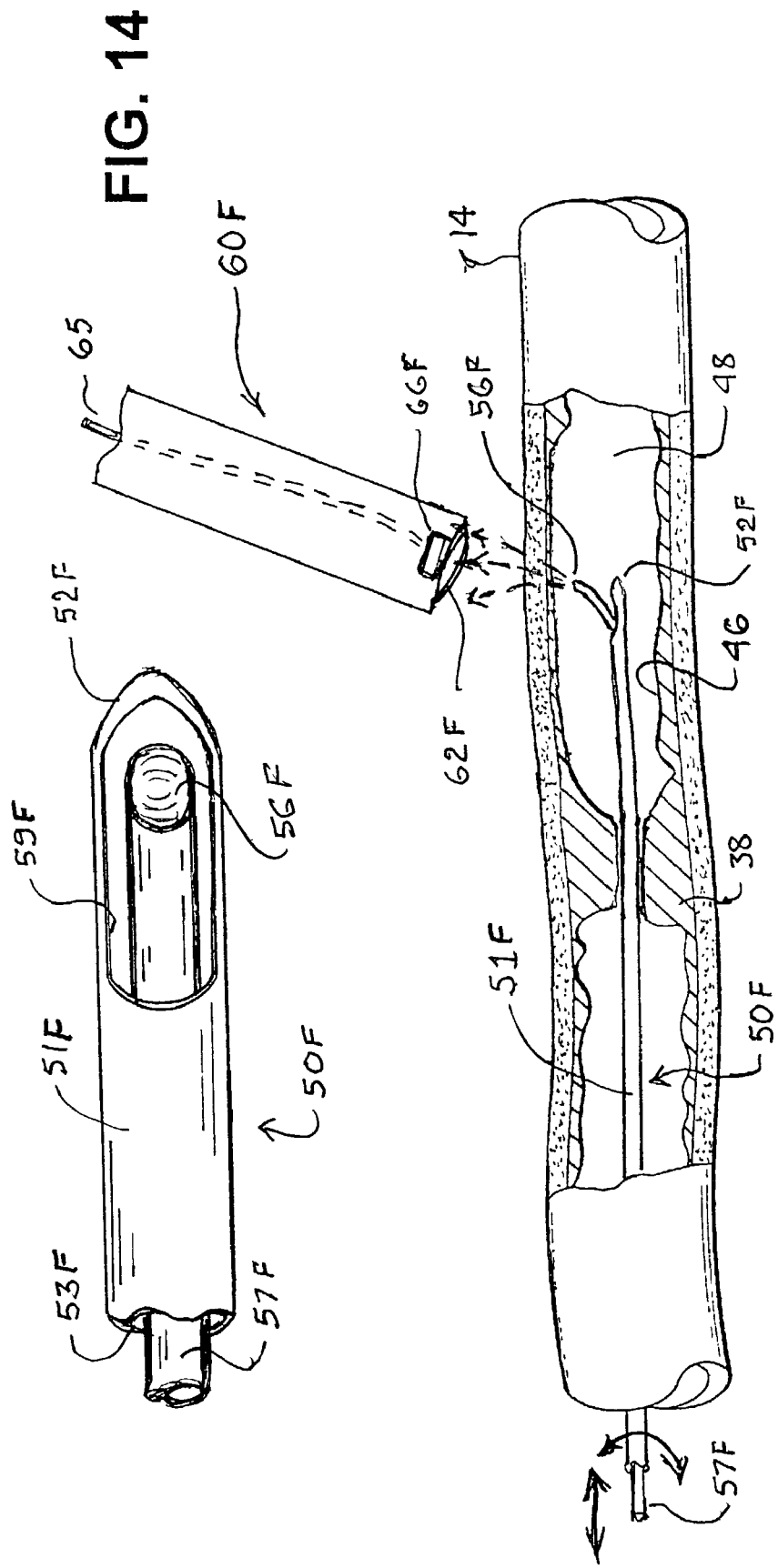

FIG. 17
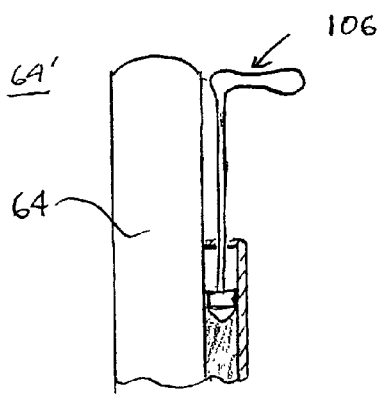
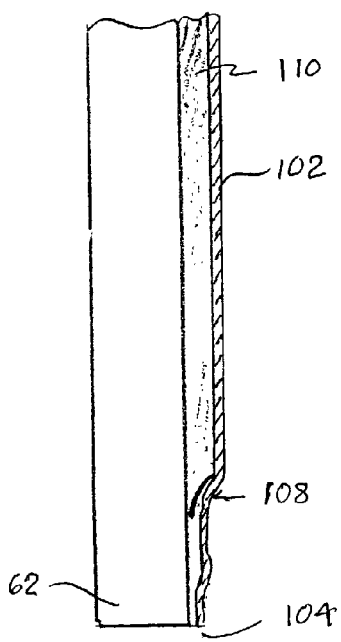
FIG. 18
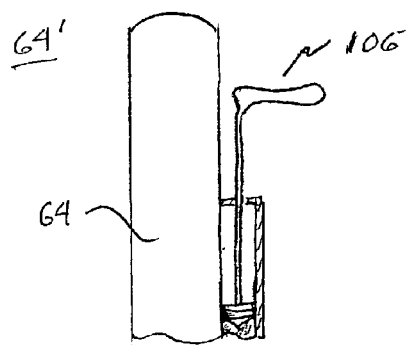
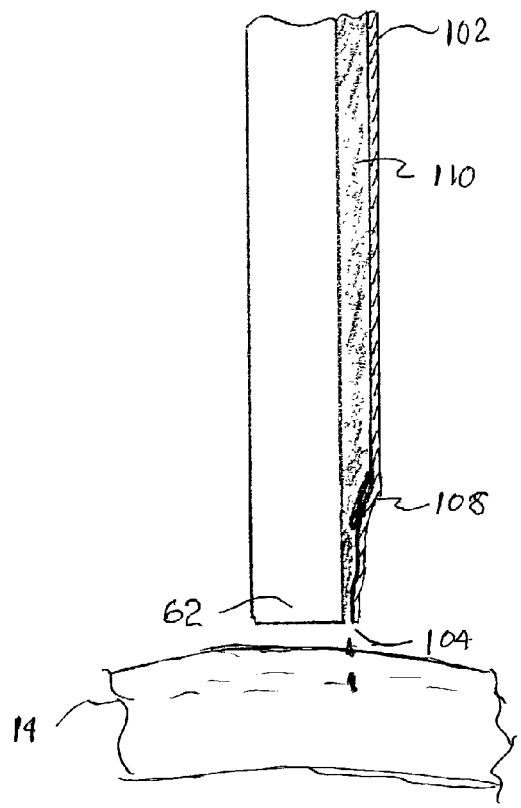

METHODS AND APPARATUS FOR LOCATING BODY VESSELS AND OCCLUSIONS IN BODY VESSELS

FIELD OF THE INVENTION

The present invention pertains to methods and apparatus employed to locate body vessels and occlusions in body vessels finding particular utility in cardiac surgery, particularly minimally invasive cardiac surgery to locate cardiac arteries and occlusions in cardiac arteries.

BACKGROUND OF THE INVENTION

Diseases of the cardiovascular system affect millions of people each year and are a leading cause of death throughout the world. The cost to society from such diseases is enormous both in terms of the number of lives lost as well as in terms of the costs associated with treating patients through traditional surgical techniques. A particularly prevalent form of cardiovascular disease is coronary artery disease (CAD), which is caused by atherosclerosis. Atherosclerosis is a disease in which the lumen (interior passage) of an artery becomes stenosed (narrowed) or even totally occluded (blocked) by an accumulation of fibrous, fatty, or calcified tissue (hereinafter referred to collectively for convenience as an occlusion). Over time, this tissue, known in medicine as an atheroma, hardens and occludes the artery. The partial stenosis or full occlusion of the coronary arteries that supply the heart muscle leads to ischemia (deficient blood flow) of the heart muscle, angina (chest pain), and can lead to infarction (heart attack) or patient death. Although drug therapies and modifications to diet and lifestyle show great promise for preventing and treating atherosclerotic vascular disease, many patients urgently require restoration of blood flow that has already been lost, especially in those having severely or totally occluded blood vessels.

In many cases, a patient suffering such a coronary vessel occlusion undergoes a coronary artery bypass graft (CABG) surgical procedure, more commonly known as a "heart bypass" operation to restore normal oxygenated blood flow to the heart muscle downstream of the occlusion. The heart bypass typically involves surgically attaching a blood vessel harvested from the patient's body from a source of oxygenated blood, e.g., the aorta or a site of the obstructed coronary artery proximal to the obstruction, to provide a conduit for oxygenated blood downstream or distal to the occlusion to restore the flow of oxygenated blood to the heart muscle. CABG surgery is generally lengthy, traumatic and subject to patient risk. Among the risk factors involved is the use of a cardiopulmonary bypass (CPB) circuit, also known as a "heart-lung machine", to both pump blood and oxygenate the blood so that the patient's heart can be stopped or arrested during the surgery, with its function performed by the CPB circuit. Recently, beating heart procedures have been developed that eliminate the need for any form of CPB.

In one approach, the surgeon harvests a section of a blood vessel from the patient's venous or arterial system, closes any branching vessel openings, and prepares its proximal and distal ends to be attached in a "proximal anastomosis" and a "distal anastomosis" bypassing the occlusion. The proximal or inflow end of such a "free graft" can be attached via a proximal anastomosis at a site proximal or upstream to the occlusion or to another vessel supplying oxygenated blood, e.g., the aorta. Generally, a free graft is a section of the saphenous vein harvested from the patient's leg or segment of radial artery harvested from the patient's arm.

In another approach, an available blood vessel within the trunk is dissected from supporting tissue while leaving it connected to the source of oxygenated blood so as to provide a source vessel free end. The sites of excision of the "attached" graft are closed to avoid blood loss, and the source vessel free end is anastomosed to the obstructed coronary artery at a distal anastomosis site distally or downstream from the occlusion that obstructs or restricts blood flow.

The trunk hosts a number of potential grafts including, the left internal mammary artery (left IMA), the right internal mammary artery (right IMA), the radial arteries and three visceral arteries, one in the abdomen, and two in the lower abdominal wall, though the latter can be quite short and are generally of limited usefulness. The visceral arteries include the epigastric artery, the gastroepiploic artery and the splenic artery.

The left IMA is best used for bypass to the left anterior descending (LAD) coronary artery and its diagonal branches, whereas, the right IMA can be used for bypass to selected vessels more posterior such as the distal right coronary artery (RCA). The right IMA can also be used for bypass to selected marginal branches of the left circumflex coronary artery. A segment of radial artery harvested from an arm is generally used to revascularize the posterior surface of the heart. The right gastroepiploic artery can be used to revascularize almost any artery on the surface of the heart and is most commonly used for bypass to the distal RCA or the posterior descending coronary artery. In unusual circumstances, the splenic artery is used to revascularize posterior coronary arteries, but it is long enough to reach the marginal branches of the circumflex coronary artery.

Surgeons typically complete bypass grafts to the following coronary arteries in a patient undergoing multiple bypass surgery in roughly the following order: posterior descending coronary artery (PDA), RCA, obtuse marginal branch, circumflex coronary artery, diagonal branch, and LAD. More generally, surgeons typically revascularize the three coronary systems in the following order: right, circumflex, and anterior descending. However, the order can vary depending on whether the procedure is performed on a beating heart or an arrested heart. About three to four bypass grafts, of which one to three are free grafts, are generally performed per procedure when the heart is arrested. In contrast, about two to three bypass grafts, of which zero to two are free grafts, are generally performed per beating heart procedure. In general, one free graft is used per beating heart procedure.

Two anastomoses are performed when a saphenous vein or other blood vessel is used as a free graft in a CABG procedure; one to the diseased artery distal to the obstruction (outflow end) and one proximally to the blood vessel supplying the oxygenated blood (inflow end). End-to-side anastomotic techniques described further herein are usually performed, although end-to-end or side-to-side anastomotic techniques described further herein are performed at times. For example, sequential graft techniques or "jump" grafts which use side-to-side anastomoses can be used to conserve the amount of blood vessels required when more than one graft is required in any of the three coronary systems for complete revascularization of the heart.

The majority of surgeons will complete the distal anastomosis of a free graft prior to completion of the proximal anastomosis. The small percentage of surgeons who do complete the proximal anastomosis first usually do so to allow antegrade perfusion of cardioplegic solution through the graft during revascularization.

Construction of an anastomosis begins by first precisely locating the occlusion within the target coronary artery. Then, the anastomosis site(s) of the target coronary artery are isolated from the epicardial tissues and overlying fatty layers. Typically, blunt, rounded #15 scalpel blades are employed to dissect these tissues and layers away from the target coronary artery. Blood flow in the target coronary artery can be interrupted by, for example, temporary ligation or clamping of the artery proximal and distal of the anastomosis site. The target coronary artery wall is opened to form an arteriotomy, that is, an elongated incision at the anastomosis site extending parallel to the axis of the coronary vessel and equally spaced from the sides of the coronary artery that are still embedded in or against the epicardium. The arteriotomy is typically created by use of a very sharp, pointed, #11 scalpel blade to perforate the target coronary artery wall, and the puncture is elongated the requisite length using scissors. The length of the incision generally approximates the diameter of the graft or source vessel, e.g., a typical incision for a saphenous vein is about 4 to 5 mm. A "perfect arteriotomy" is an incision that has straight edges, that does not stray from the axial alignment and equal distance from the sides of the coronary artery, and is of the requisite length. A variety of techniques and devices may be used to form an arteriotomy and/or aortotomy, i.e., an incision in the aorta. For example, devices that can cut tissue may be used to form an incision in a vessel. Devices that can cut tissue include mechanical devices, e.g., scissors, scalpel, knife or punch, radio frequency (RF) devices, e.g., electrocautery devices, laser devices and ultrasound devices.

Next, it is necessary to prepare the attachment end or ends of the graft or source vessel by cutting the source vessel end to an appropriate angle for an end-to-side anastomosis or by closing the source vessel end and forming an elongated arteriotomy in the source vessel wall of a suitable length that is axially aligned with the source vessel axis for a side-to-side anastomosis. In an end-to-side anastomosis, it is necessary to prepare the attachment end of the source vessel by beveling its severed end typically at about 30 to 45 degrees. Generally, the surgeon uses surgical scalpels and scissors to shape the source vessel end or make the elongated arteriotomy slit in the source vessel, and sutures to close the open severed end. One method of forming an elongated arteriotomy of a suitable length axially aligned with the source vessel axis for a side-to-side anastomosis is shown, for example, in U.S. Pat. No. 5,893, 369.

The prepared end or elongated arteriotomy slit of the bypass graft or source vessel is attached or anastomosed to the target coronary artery at the arteriotomy in a manner that prevents leakage of blood. The inner, endothelial layer, vessel linings are less thrombogenic than the outer epithelial layers. So, in one approach, the attachment of graft to target artery is made by everting and applying the interior linings of the bypass graft or source vessel and the target coronary artery against one another and suturing the everted linings together. Surgeons can construct the anastomosis via a ten-stitch running suture using 7-0 polypropylene suture material. The ten-stitch anastomosis typically comprises five stitches around the "heel" of the source vessel and five stitches around the "toe" of the source vessel. The five stitches around the heel of the graft comprise two stitches to one side of the apex of the graft and the artery, a stitch through the apex and two stitches placed at the opposite side of the apex. The graft is generally held apart from the coronary artery while the stitches are constructed using a needle manipulated by a forceps. Suture loops are drawn up and the suture pulled straight through to eliminate purse-string effect. The five stitches around the toe of the graft also comprise two stitches to one side of the apex of the graft and the artery, a stitch through the apex and two stitches placed at the opposite side of the apex. Again, suture loops are drawn up, the suture is pulled straight through to eliminate purse-string effect, and the suture ends are tied.

The proximal anastomosis of a saphenous vein free graft to the aorta, i.e., an aortosaphenous vein anastomosis, is formed by first removing the pericardial layer that covers the aorta. An occluding or side-biting clamp can be placed on the aorta at the anastomosis site. A small circular or elliptical portion of the ascending aorta is excised forming a small opening, or aortotomy, 4 to 5 mm in diameter. An aortic punch typically facilitates this procedure. The opening for a right-sided free graft is made anterior or to the right lateral side of the aorta, whereas an opening for a left-sided free graft is made to the left lateral side of the aorta. The opening is made proximal on the aorta if the free graft is to supply blood to the right coronary artery. If the free graft is to supply blood to the anterior descending coronary artery, the opening is made in the middle on the aorta. And, if the free graft is to supply blood to the circumflex artery, the opening is made distal on the aorta. The right graft opening is placed slightly in the right of the anterior midpoint of the aorta and the left graft opening slightly to the left. The end of the saphenous vein free graft is cut back longitudinally for a distance of approximately 1 cm. A vascular clamp is placed across the tip of the saphenous vein free graph to flatten it, thereby exposing the apex of the vein. Five suture loops of a running suture using 5-0 polypropylene are then placed around the heel of the saphenous vein free graft and passed through the aortic wall. Two stitches are placed on one side of the apex, the third stitch is placed precisely through the apex of the incision in the saphenous vein free graft, and the final two stitches are placed on the opposite side of the apex. Suture traction is used to help expose the edge of the aortic opening to ensure accurate needle placement. Stitches include about 3 to 5 mm of the aortic wall for adequate strength. Suture loops are then pulled up to approximate the vein graft to the aorta. The remaining stitches are placed in a cartwheel fashion around the aortic opening thereby completing the remainder of the anastomosis.

Left-sided grafts are oriented so the apex of the incision in the heel of the saphenous vein free graft will face directly to the left side. The stitches are placed in a clockwise fashion around the heel of the graft and in a counterclockwise fashion around the aortic opening. Right-sided grafts are oriented in a caudal fashion. The stitches are placed in a counterclockwise fashion around the heel of the graft and in a clockwise fashion around the aortic opening. Five suture loops complete the heel portion of the graft and an additional five or six are necessary to complete the toe of the graft. Finished proximal anastomoses tend to have a "cobra-head" appearance.

It is essential for the surgeon to take steps to minimize the possibility of thrombosis, narrowing and/or premature closure of the anastomosis due to technical errors. Some surgeons feel the proximal anastomosis must have a take-off angle of 45 degrees while other surgeons believe the take-off angle is not critical. In addition, it was felt that intima-to-intima contact of the vessels at the anastomosis was critical for endothelization to occur, thereby making an ideal union of the vessels. However, most surgeons now feel intima-to-adventitia contact is acceptable. The main objective of the surgeon is to create an anastomosis with an expected long-term patency rate of greater than 5 to 10 years. The creation of an anastomosis takes approximately 10-15 minutes.

Adequate exposure that affords acute visualization of the vessel walls is an essential requirement for creating a sutured anastomosis without error. Acute visualization of the vessel walls is mandatory in order to properly place each stitch and avoid inadvertently including the back wall of the vessel in a stitch, which in effect narrows or completely occludes the vessel. Most surgeons employ blood-less field devices such as shunts, snares, and misted blowers to achieve the required exposure.

Currently, manual suturing is the gold standard for creation of a vascular anastomosis. However, a number of cardiac surgical procedures, e.g., off-pump, beating heart CABG procedures, minimally invasive procedures and even totally endoscopic procedures with access through ports only, can require a variety of other anastomotic techniques. Avoiding the use of cross clamps and CPB or dramatically reducing pump run and cross clamp times can effectively minimize post-operative complications. For this reason, surgeons have been increasingly using easier, quicker, less damaging, but reliable automated, semi-automated, or at least facilitated methods to replace or enhance the normal process of a manually sutured vascular anastomosis.

The major objective of any CABG procedure is to perform a technically perfect anastomosis. However, creation of a technically perfect anastomosis is generally complex, tedious, time consuming and its success is highly dependent on a surgeon's skill level. Therefore, it is perceived that creation of vascular anastomoses without the need to perform delicate and intricate suture lines may enable surgeons to more quickly create simpler and effective anastomoses. Currently, a number of mechanical anastomotic devices, materials, techniques, and procedures are being developed for facilitating the process of forming an anastomosis including vascular clips or staplers, glues, adhesives or sealants, laser welding, mechanical couplers, stents and robot-assisted suturing. These techniques are being developed for performing end-to-end, end-to-side and/or side-to-side anastomoses with or without temporary blood flow interruption. In general, these techniques can include the use of various biomaterials and/or biocompatible agents. See, for example, U.S. Pat. Nos. 5,385,606, 5,695,504, 5,707,380, 5,972,017 and 5,976,178, and 6,231,565.

Sealants, adhesives or glues used in creation of vascular anastomoses are generally based on synthetic or biological substances or a combination of both that are used to either seal post-operative internal air or fluid leaks, or to close a topical wound. Surgical sealants are generally absorbable materials used primarily to control internal bleeding and to seal tissue. Surgical adhesives are stronger than sealants, are often non-absorbable, and typically are biologically based. Surgical glues are stronger than surgical adhesives, are often synthetic and non-absorbable, and are often used to close topical wounds. Surgical glues are typically made from cyanoacrylate adhesives that form strong tissue-to-tissue bonds and are used to bond a wide variety of materials. Biologically based sealants, adhesives or glues are generally derived from blood clotting components such as proteins (e.g., fibrinogen or fibrin), enzymes (e.g., thrombin) and/or platelets. Fibrin based sealants, adhesives or glues generally combine the protein fibrinogen with the enzyme thrombin to immediately begin the clotting process. One surgical adhesive currently being marketed includes a combination of collagen (proteins which form fibers to support body tissues), formalin (a form of formaldehyde), resorcinol and glutaraldehyde. Some sealants, adhesives or glues can be used to control bleeding or to reinforce suture or staple lines rather than to make tissues adhere, thus functioning more as hemostatic agents than glues.

There are a number of uses for sealants, adhesives or glues, such as replacement for sutures and staples in minimally invasive procedures, where the surgeon has little room to maneuver, or for the repair of aortic dissections, where the tissue is so thin it can be damaged by sutures. Such sealants, adhesives or glues can also be used for anastomotic sealing, in which the seal should not be absorbed, or carotid patching, where a complete seal is desired.

Laser welding techniques using laser energy emitted by $CO_2$ lasers, argon lasers or Neodymium-YAG lasers, for example, which thermally join tissues together can also be used to create the anastomosis between the source vessel and coronary artery tissues. One possible mechanism of laser welding of tissues is the thermal denaturation and coagulation of collagen fibrils in the tissue, which generally occur above 60° C. Photosensitive dyes (e.g., indocyanine green) that absorb the laser energy can be applied to the tissues to be joined at the weld site to enhance the weld strength while minimizing thermal damage to the surrounding tissue. Photosensitive dyes used in laser welding procedures may or may not bind chemically to the tissue's proteins depending on their chemical structure. Laser welding can provide a watertight seal to hold bodily fluids in, thereby preventing blood loss, infections and repeat surgeries. Alternatively, a "solder" comprising synthetic and/or biological components that absorb the laser energy can be applied to the tissues to be joined at the weld site to enhance the weld strength while minimizing thermal damage to the surrounding tissue. For example, proteins such as albumin have been used in various solder formulations. Laser welding devices can include one or more flexible optical fibers and solder-delivery tubes that can be snaked through small ports or through a channel in an endoscope.

Mechanical anastomotic devices include stapling devices, clipping devices, ring and pin coupling devices, and suturing devices. These anastomotic devices can be automated or semi-automated. Mechanical anastomotic devices also include mechanical couplers including stents, ferrules, and/or rings. Materials used to form an anastomosis via a mechanical device and/or coupler must be biocompatible, bio-absorbable, bio-active and/or bio-inert.

One component intra-luminal mechanical coupling devices are generally stent-like in design. The graft and the target vessel, i.e., the aorta or coronary artery, are forced into tubular shapes by the device. In general, the application of this type of device is relatively easy. The device can be made to unfold by itself so no deformation forces are necessary at the anastomosis. In addition, angled anastomoses are possible. The device can however have a lot of foreign material exposed within the blood stream, thus increasing the risk of stenosis and thrombosis. In some cases, the device can prevent direct contact between the graft and the target vessel, thereby preventing the vessel walls from healing together. Intimal damage to both the graft and the target vessel can also occur during delivery of the device. Extra sealing methods, e.g., tissue sealants, may be necessary to provide a leak-free anastomosis. In addition, the size of the device is strongly related to the size of the vessels. Therefore, a range of devices and measurement of the vessels is necessary.

Two component intra-luminal mechanical coupling devices require both the graft and the target vessel to be connected to their own coupling component, after which the two coupling components are connected to each other, thereby forming the complete anastomosis. Problems associated with construction of an anastomosis using a two component intra-luminal mechanical coupling device can include mounting of the vessels and connection of the components. Tools for mounting the individual coupling components to each vessel and tools for connecting the coupling components together are both generally required.

One component, extra-luminal, mechanical coupling devices typically allow direct intima-to-intima contact and typically require a delivery tool to position the coupling device in the recipient vessel. In addition, this type of device present less foreign material in the blood stream, thereby decreasing the risk of stenosis and thrombosis. However, mounting of the graft to the coupling device may not be easy. Damage can occur to the intimal layer when everting the graft onto the device for two reasons: 1) one tip of a pair of pincers used to solidly grab vessel wall to evert an artery will roughly touch and pinch the intima of the artery; and, 2) eversion causes high strain (stretching) that can damage the arterial wall. A high level of surgical skill and experience is necessary to reduce the probability that such damage occurs. The skilled surgeon must estimate where to grab the vessel wall and how to evert the graft onto the device to obtain a symmetrical anastomosis. A specially designed mounting tool can make the step of mounting the graft onto the coupling device easier and can help to minimize damage to the graft. In addition, care must be taken to avoid compression of tissue by the coupling device since compression can cause pressure necrosis.

Two component extra-luminal mechanical coupling devices, like the two component intra-luminal mechanical coupling devices, require both the graft and the target vessel to be connected to their own coupling component, after which the two coupling components are connected to each other, thereby forming the complete anastomosis. Problems associated with construction of an anastomosis using a two component extra-luminal mechanical coupling device also include mounting of the vessels and connection of the components. Tools for mounting the individual coupling components to each vessel and tools for connecting the coupling components together are both generally required. Hybrid anastomosis techniques combine one or more techniques, e.g., sutures or clips with glues or laser welding. A specific example of a hybrid anastomotic technique is the use of an intraluminal stent-like device combined with an extraluminal application of biological glue.

Various types of artificial biocompatible reinforcement sleeves or rings, e.g., those shown in the above-referenced '369 patent can be used in the anastomosis. Other examples of forming the arteriotomy, the shaped end or side wall of the source vessel, and the positioning and attachment of the source vessel and target artery together are set forth in U.S. Pat. Nos. 5,799,661, 5,868,770, 6,026,814, 6,071,295, 6,248,117, and 6,332,468.

Largely invasive surgical techniques are typically employed to provide the surgeon access to the anastomoses sites. For this reason, CABG surgery is generally performed through a median sternotomy (open-chest surgical exposure). A median sternotomy incision begins just below the sternal notch and extends slightly below the xyphoid process. A sternal retractor is used to separate the sternal edges for optimal exposure of the heart. Hemostasis of the sternal edges is typically obtained using electrocautery with a ball-tip electrode and a thin layer of bone wax.

Typically, fat layers that make it difficult to see either the artery or the occlusion cover the epicardial surface and the obstructed cardiac artery. However, surgeons are able to dissect the fat away to expose the artery and manually palpate the heart to feel the relatively stiff or rigid occlusion within the artery as a result of their training and experience. The surgeon can determine the location and length of the occlusion as well as suitable sites of the target coronary artery for the proximal and distal anastomoses with some degree of success. However, it is difficult to accurately determine the bounds of a soft or "cheesy" occlusion, and mistakes can happen.

The open chest procedure involves making a 20 to 25 cm incision in the chest of the patient, severing the sternum and cutting and peeling back various layers of tissue in order to give access to the heart and arterial sources. As a result, these operations typically require large numbers of sutures or staples to close the incision and 5 to 10 wire hooks to keep the severed sternum together. Such surgery often carries additional complications such as instability of the sternum, post-operative bleeding, and mediastinal infection. The thoracic muscle and ribs are also severely traumatized, and the healing process results in an unattractive scar. Post-operatively, most patients endure significant pain and must forego work or strenuous activity for a long recovery period.

Many minimally invasive surgical techniques and devices have been introduced in order to reduce the risk of morbidity, expense, trauma, patient mortality, infection, and other complications associated with open-chest cardiac surgery. Less traumatic limited open chest techniques using an abdominal (sub-xyphoid) approach or, alternatively, a "Chamberlain" incision (an approximately 8 cm incision at the sternocostal junction), have been developed to lessen the operating area and the associated complications. In recent years, a growing number of surgeons have begun performing CABG procedures using minimally invasive direct coronary artery bypass grafting (MIDCAB) surgical techniques and devices. Using the MIDCAB method, the heart typically is accessed through a mini-thoracotomy (e.g., a 6 to 8 cm incision between a patient's ribs or intercostal space) that avoids the sternal splitting incision of conventional cardiac surgery. A MIDCAB technique for performing a CABG procedure is described in U.S. Pat. No. 5,875,782, for example.

Other minimally invasive, percutaneous, coronary surgical procedures have been advanced that employ multiple small trans-thoracic incisions to and through the pericardium, instruments advanced through ports inserted in the incisions, and a thoracoscope to view the accessed cardiac site while the procedure is performed as shown, for example, in the above-referenced '468 patent and in U.S. Pat. Nos. 5,464,447, and 5,716,392. Surgical trocars having a diameter of about 3 mm to 15 mm are fitted into lumens of tubular trocar sleeves, cannulae or ports, and the assemblies are inserted into skin incisions. The trocar tip is advanced to puncture the abdomen or chest to reach the pericardium, and the trocar is then withdrawn leaving the port in place. Surgical instruments and other devices such as fiber optic thoracoscopes can be inserted into the body cavity through the port lumens. As stated in the '468 patent, instruments advanced through trocars can include electrosurgical tools, graspers, forceps, scalpels, electrocauteries, clip appliers, scissors, etc.

In such procedures, the surgeon can stop the heart by utilizing a series of internal catheters to stop blood flow through the aorta and to administer cardioplegia solution. The endoscopic approach utilizes groin cannulation to establish CPB and an intraaortic balloon catheter that functions as an internal aortic clamp by means of an expandable balloon at its distal end used to occlude blood flow in the ascending aorta. A full description of an example of one preferred endoscopic technique is found in U.S. Pat. No. 5,452,733, for example.

However, recently developed, beating heart procedures eliminate the need for any form of CPB, the extensive surgical procedures necessary to connect the patient to a CPB machine, and to stop the heart. These beating heart procedures can be performed on a heart exposed in a full or limited thoracotomy or accessed percutaneously.

In such percutaneous procedures, the epicardium of the beating or stopped heart is exposed for viewing typically by use of grasping and cutting instruments inserted through a port to cut through the pericardium surrounding the heart while the area is viewed through a thoracoscope or endoscope, e.g., inserted through a different port. Once the heart is exposed, it is necessary to locate the target coronary artery as well as the occlusion. In this case, it is not possible for the physician to manually palpate the fatty tissue overlying the artery and occlusion to accomplish this.

Fluoroscopy is widely employed during coronary catheterization to provide a real-time X-ray image to visualize the position of devices advanced within the vascular system of a patient. Bi-plane fluoroscopy, provides two real-time x-ray images acquired from different angles to visualize a totally occluded coronary artery. However, biplane fluoroscopy is costly and slow, and erroneous interpretation of the images often occurs.

A reliable technique is needed for precisely determining the relative positions of a therapeutic working device, the boundaries of an occlusion, and the structure of the occluded artery as the working device is manipulated or otherwise. Therefore, it has been proposed to employ instruments, e.g. catheters and guidewires, that can be advanced either through the artery lumen and the occlusion in the target coronary artery itself or via a percutaneous port lumen, or both, to identify suitable unobstructed sites of the target coronary artery for proximal and/or distal anastomoses.

A hand held probe is disclosed in U.S. Pat. No. 6,248,072 that is adapted to be advanced against the epicardium by the surgeon to determine the location of the target coronary artery and the occlusion within the arterial lumen. The probe incorporates an ultrasound transducer at the probe end in contact with the heart that emits and receives reflected ultrasound signals. The reflected ultrasound signals are processed in external equipment to develop images indicative of the tissue that the transducer is applied to by the physician. It is implied that unobstructed anastomosis sites can be determined by the characteristic display of an ultrasound image of an open arterial lumen. The physician may mistakenly locate and open the wrong vasculature lumen unless the physician knows approximately where the target coronary artery resides, because the probe only identifies lumens from cardiac tissue. In fact, it can be difficult to distinguish between a lumen of an artery and that of a vein. Smaller vessel diameters can also be harder to identify than larger diameter vessels. It appears the probe would be unable to precisely identify the targeted coronary artery. Further, in a closed-chest procedure, it can sometimes be very difficult to identify a specific area of the heart while viewing the heart with an endoscope having a limited field of view thereby making it difficult to precisely locate the targeted vessel.

The use of intravascular ultrasound catheters having distally disposed ultrasonic transducers is disclosed in U.S. Pat. No. 6,026,814. The '814 patent relates to systems for performing CABG almost entirely employing intravascular catheters and devices. In one embodiment of the '814 patent, a first ultrasound catheter is advanced from a surgically created opening in a peripheral artery, e.g., the femoral artery, to and through the occlusion in the target coronary artery to a distal anastomosis site. A second ultrasound catheter is advanced in a similar fashion into the lumen of the source vessel to locate a further ultrasound transducer at the site where the source vessel is to be anastomosed to the distal anastomosis site of the cardiac artery. The ultrasound transducers act as transmitters and receivers in order to guide the distal end of the source vessel to the distal anastomosis site. Instruments that are advanced through the source vessel are used to perform the arteriotomy in the target coronary artery at the distal anastomosis site and to anastomose the target coronary artery to the source vessel. According to the '814 patent, one of the ultrasound transducers is positioned in the lumen of the source vessel while the other is positioned in the target vessel. Therefore, the size of the vessels, i.e. the diameter of the vessels, will dictate the size or diameter of the ultrasound transducers or other types of transmitters and receivers. The '814 patent does suggest that a number of other cooperating transmitters and receivers, e.g., RF signal transmitter and receiver, one or more point light source and photodiode, electromagnet and magnetic field responsive element can be substituted for the ultrasound transmitter and receiver. However, these transmitters and receivers will be limited in size required to fit in a source vessel or a target vessel. The smaller size may limit the effectiveness of the transmitters and receivers. For example, the size of an ultrasound transducer can limit the distance and resolution that images may be acquired. Further, the length of the source vessel must be determined prior to guiding of the distal end of the source vessel to the distal anastomosis site. Therefore, the physician would need to know the exact length the source vessel must be prior to guiding of the vessel. If the physician chooses the wrong length, the source vessel may end up to short or to long, both of which may be detrimental to the creation of the anastomosis. In addition, it may be very difficult to manipulate and guide the source vessel having an ultrasound transducer inside itself to the target vessel.

The use of a hand held ultrasound instrument and system to pass a relatively stiff distal segment guidewire through a hardened obstruction that cannot be crossed by the typical soft tip guidewire is disclosed in U.S. Pat. No. 6,241,667. Typically, a guidewire is advanced from a surgically created opening in a peripheral artery, e.g., the femoral artery, to the occlusion in the target coronary artery and the guidewire (or a catheter advanced over the guidewire) is advanced through the occlusion. This approach of placing a variety of devices for performing procedures in the arterial system, e.g., at the occlusion, is well known in the field of interventional cardiology. The guidewire is maneuvered into place to act as a guide for positioning the placement of catheters or devices "over the wire." The guidewire outer diameter typically ranges from 0.010 to 0.038 inches whereas an interventional catheter lumen diameter typically ranges from 0.040 to 0.25 inches so that a combination of guidewire and interventional catheter can be selected that suits the vascular lumens of a particular vascular pathway.

In one embodiment of the '667 patent, an imaging locator comprising an imaging tube and an ultrasonic transducer is passed through an incision in the chest of a patient and positioned adjacent the surface of the heart and outside an occluded coronary artery. A catheter having a tissue-penetrating working element is disposed in the catheter delivery lumen of the imaging tube. During operation, the working element is advanced from the catheter delivery lumen and steered and manipulated through the arterial wall distal to the occlusion and advanced proximally to cross the occlusion retrograde while being imaged by the imaging locator. A guide catheter is then advanced from a surgically created opening in a peripheral artery, e.g., the femoral artery, to the proximal or upstream side of the occlusion in the target coronary artery. The working element is then advanced into the lumen of the guide catheter until it can be grasped outside the body, whereupon the guide catheter is removed.

Again, the physician may mistakenly locate and open the wrong vasculature lumen unless the physician knows approximately where the target coronary artery resides, and it may be difficult to distinguish between a lumen of an artery and that of a vein. Smaller diameter vessels may also be harder to identify than larger diameter vessels. Therefore, the imaging locator alone may be unable to precisely identify the targeted coronary artery. Furthermore, in a closed-chest procedure it can sometimes be very difficult to identify a specific area of the heart while viewing the heart with an endoscope having a limited field of view thereby making it difficult to precisely locate the targeted vessel.

U.S. Pat. Nos. 5,722,426, 6,080,175 and 6,113,588 disclose the use of light emission to assist in locating an occlusion in a target coronary artery by illuminating the arterial lumen with light that the surgeon can observe through a thoracoscope or directly when the epicardial surface is exposed to view in a thoracotomy. A hand held probe is disclosed in the '426 patent that is adapted to be inserted through an incision made in the target coronary artery upstream or downstream from the occlusion and advanced toward the occlusion to determine its respective upstream or downstream end. The probe incorporates a plurality of light sources along the probe end that emit light as the probe is advanced. It is asserted that the light can be seen through the vessel wall and that the light brightness is attenuated as the probe penetrates the occlusion. Unobstructed anastomosis sites can be determined by viewing the change in light brightness. Catheter borne light emitters are disclosed in the '175 and '588 patents. Again a catheter is advanced from a surgically created opening in a peripheral artery, e.g., the femoral artery, to and through the occlusion in the target coronary artery to a distal anastomosis site. The light transmitted through the arterial wall is observed, and it is asserted that unobstructed anastomosis sites can be determined by viewing the change in light brightness.

However, the ability of a surgeon to visually ascertain changes in light brightness of a light shining through a vessel wall either directly or through a thoracoscope can be hampered if the light is diffused in the tissue of the vessel wall or is blocked by an obstruction or any fatty tissue overlying the blood vessel and epicardium. The thickness of cardiac tissue and fatty deposits located between the coronary artery and the surface of the heart can vary greatly among patients. This variance in tissue thickness and fatty deposits can effective a surgeon's ability to accurately identify unobstructed anastomosis sites, since the surgeon's ability to visually ascertain changes in light brightness shining through a vessel wall can be diminished. Moreover, environmental conditions of the operating room, particularly the brightness of the room or the surgical field, can diminish the brightness of the transmitted light and make it difficult to see.

A further probe, referred to as the "H-Probe", is described by Verimetra, Inc. at www.verimetra.com/MEMS_Sensors_for_Surgery/H-Probe/h-prove.html. The H-Probe is described as a MEMS-based instrument designed to palpate vessels to determine the position of internal plaque. It is asserted that the MEMS-based vessel hardness H-Probe at the end of an MIS tool will minimize, if not eliminate, erroneous choices for bypass procedure location, leading to reduced post-operative complications.

While these approaches may hold promise, in some instances they are either unduly complicated to practice or not specific enough. Simple devices and methods that can positively identify vessels and suitable anastomosis sites with high specificity remain highly desirable. Such devices and methods would be useful in locating or tracking body vessels exposed in a surgical field but obstructed by overlying tissues.

SUMMARY OF THE INVENTION

In accordance with the present invention, an elongated vessel lumen probe is advanced into the lumen of a body vessel to locate a vessel lumen probe element at or near the distal end of the vessel lumen probe in the area where the vessel or an occlusion of the vessel lumen is expected to be located. If the vessel is occluded, the vessel lumen probe can be advanced, if possible, through the occlusion to position the vessel lumen probe element downstream from the occlusion. A vessel surface probe having a vessel surface probe element sensor at the surface probe distal end interacts with the lumen probe element to determine the location of the vessel lumen probe element and thereby determine the location of the body vessel.

The vessel surface probe element sensor is moved about against the tissue over the suspected location of the vessel of interest until a vessel surface probe element sensor of the present invention at the vessel surface probe distal end interacts with the vessel lumen probe. A predetermined interaction between the vessel lumen probe and the vessel surface probe is discerned when the vessel surface probe element sensor is minimally separated from the vessel lumen probe element. Therefore, the vessel lumen probe and the vessel surface probe can be employed to map the location of the vessel as the vessel lumen probe element is advanced through the vessel. The vessel surface probe can be used to follow the progress of the distal end of the vessel lumen probe, e.g., as it approaches and is advanced through or is blocked by an occlusion.

The vessel lumen probe distal end can be biased to extend toward the vessel wall when it is advanced through the vessel. The vessel lumen probe distal end can be rotatable to sweep the vessel lumen probe around the vessel wall within the vessel lumen to locate the vessel identifying distal end closest or furthest to the vessel surface probe. In one embodiment, the distal end of the vessel lumen probe is adapted to be rotated from the proximal vessel identifying end or rotates or moves under the influence of the vessel surface probe so that the distal end of the vessel lumen probe can be directed as close as possible toward the vessel wall nearest the vessel surface probe or as far away as possible towards the vessel wall furthest away from the vessel surface probe while the vessel surface probe is applied by and moved about the tissue surface over the vessel wall.

In one embodiment, the vessel lumen probe element can be moved back and forth in the vessel lumen through obstructed and unobstructed portions while the strength of the interaction between the vessel surface probe element sensor and the vessel lumen probe element is monitored. It is expected that the strength would be reduced when the vessel lumen probe element traverses a vessel obstruction that forces the vessel lumen probe element further away from the vessel wall and that the reduction can be perceived.

In one embodiment, the predetermined interaction comprises magnetic field interaction that attracts or repels the vessel lumen probe element toward or away from the vessel surface probe element sensor as the vessel surface probe element sensor is moved over the tissue surface covering the vessel of interest. The vessel surface probe element sensor preferably comprises a high field strength miniaturized permanent magnet oriented to direct a magnetic field into the tissue and vessel lumen. The vessel lumen probe distal end element comprises a magnetic field responsive element or magnet that is drawn toward or away the vessel wall by the magnetic field. The surgeon can feel the increased strength of the magnetic field force between the vessel surface probe element sensor and the vessel lumen probe element when the vessel surface probe element sensor is brought into proximity with the vessel lumen probe element.

In a further embodiment, an electrical signal is developed having a magnitude that is proportional to the proximity of the vessel lumen probe element to the vessel surface probe element sensor. The surgeon can observe a visual display of the signal or listen to audibly reproduced signal frequencies that vary as a function of the distance between the vessel surface probe element and the vessel lumen probe sensor. For example, a maximum or target amplitude or frequency of the electrical signal is attained when the vessel surface probe element sensor and the vessel lumen probe element are separated apart by a minimal distance, e.g., the thickness of the vessel wall.

In one variation of this embodiment, the vessel surface probe element sensor and the vessel lumen probe element each comprise a conductive electrode. A low amplitude current is applied between electrodes, and the voltage is measured between the vessel surface probe and the vessel lumen probe. The measured voltage varies as a function of the impedance between the electrodes that is dictated by the intervening thickness of the vessel wall and any overlying tissue and obstructive plaque. In a further variation of this embodiment, the vessel lumen probe element is metallic, and the vessel surface probe element sensor comprises a metal detector that develops a signal varying in frequency that can be displayed on a visual display or audibly reproduced as a frequency varying with distance.

In a still further embodiment, the vessel lumen probe element comprises a light emitter, e.g. a light conducting fiber or pipe, which is coupled to a light source. The light pipe can be movable axially within a light pipe sheath lumen having a distal sheath lumen opening. The light pipe and light pipe sheath are introduced into the body vessel. The light pipe can be axially moved out of the distal sheath opening so that the light beam emitted from the light pipe distal end is selectively directed toward the vessel wall unless constrained by an occlusion. The light pipe and light pipe sheath can be rotated to sweep the emitted light about the vessel lumen so that the light can be directed outward through the vessel wall and any overlying tissues obscuring the vessel from direct view.

The vessel surface probe element sensor comprises a photosensor that develops or modulates an electrical signal proportional to the intensity of light emitted by the light pipe distal end that strikes the photosensor. The light pipe distal end is aimed outward from the light pipe sheath distal opening by manipulation of the proximal end portions of the light pipe sheath and the light pipe. The emitted light that is directed toward and impinges upon the photosensor has a magnitude that is proportional to the density of tissue and any plaque between the photosensor and the light pipe distal end. The surgeon can observe a visual display of the signal and/or listen to audibly reproduced signal frequencies that vary as a function of the light intensity. For example, a maximum or target amplitude or frequency of the electrical signal that is attained when the photosensor and the light pipe distal end are aligned and the vessel lumen is minimally obstructed by plaque.

If the outer surface exposed in the surgical field can be observed by the surgeon directly or employing an endoscope or the like, it may be possible for the surgeon to observe the emitted light direction and intensity. Consequently, this embodiment of the vessel lumen probe can have a second utility independent of interaction with the photosensor.

The light pipe can be coupled to a laser light source for creating an incision in the vessel wall. Laser light transmitted along the light pipe can be selectively directed toward the vessel wall. The laser energy emitted by the light pipe cuts into vessel wall by photo-ablation, thereby creating an opening or arteriotomy in the vessel wall. Following creation of the arteriotomy, a graft may be anastomosed at the site of the arteriotomy by use one or more sutures, staples, rings, clips, sleeves, stents, couplers, sealants, glues, and/or adhesives. In addition, a robot or laser welding technique may be used during creation of the anastomosis. Laser energy emitted by the light pipe can be used to thermally join tissues together to create an anastomosis, for example, between a graft vessel and a coronary artery. As described above, photosensitive dyes and/or solders may be used in the process. In a further variation of the invention, any of the above-described vessel surface probes can include a marker for marking the identified vessel wall or tissue overlying the identified body vessel with a biocompatible ink, e.g., a biocompatible fluorescent tissue ink.

In one preferred use of these various embodiments of the invention, the vessel lumen probe element is introduced into the lumen of an artery or vein of interest, and a surface probe element sensor can be applied against tissue over the suspected location of the artery or vein of interest in order to identify and track the artery or vessel. A surgical procedure can be safely undertaken, e.g., any of the above-described CABG procedures, when the target artery and/or the occlusion therein are identified in this manner.

These various embodiments of the present invention can also be of use in medical or surgical procedures that require avoidance of certain body vessels or body lumens that are accessible to both the vessel lumen probe and the location probe. For example, the procedure of implanting an epicardial lead requires the physician to know where the coronary vessels are located on the heart so as not to puncture a vessel during the lead implantation procedure. The delivery of cells, genes, drugs or other biological agents into the heart also can require the physician to know where the coronary vessels are located on the heart so as not to puncture a vessel during the delivery procedure. The ablation of cardiac tissue, for example, in a MAZE ablation procedure can also require vessel identification and location to prevent shrinkage or stenosis of the vessel or vessels during the ablation procedure.

These various embodiments of the present invention can also be of use in body vessel harvesting procedures that require identification and tracking of a vessel that is accessible to both the vessel lumen probe and the location probe. For example, the vessel lumen probe element can be introduced into the lumen of an internal mammary artery, right or left, and the surface probe element sensor can be applied against tissue over the suspected location of the artery in order to identify and track the artery during the vessel harvest procedure. Similarly, other body vessels can be harvested while using various embodiments of the present invention.

While the present invention finds particular utility in minimally invasive surgical procedures, it will be realized that it can be advantageously employed in other surgical procedures where the surgical field is fully accessible.

This summary of the invention has been presented here simply to point out some of the ways that the invention overcomes difficulties presented in the prior art and to distinguish the invention from the prior art and is not intended to operate in any manner as a limitation on the interpretation of claims that are presented initially in the patent application and that are ultimately granted.

BRIEF DESCRIPTION OF THE DRAWINGS

These and other advantages and features of the present invention will be more readily understood from the following detailed description of the preferred embodiments thereof, when considered in conjunction with the drawings, in which like reference numerals indicate identical structures throughout the several views, and wherein:

FIG. 9 is a side view in partial cross-section of a third embodiment of a vessel surface probe that can be percutaneously employed in conjunction with a third embodiment of a vessel lumen probe traversing an arterial occlusion to ascertain the boundaries of the obstruction by magnetic field attraction between magnets of the vessel surface probe and the vessel lumen probe;

FIG. 10 is an expanded detail side view in partial cross-section of the distal segment of the vessel lumen probe of FIG. 9;

FIG. 11 is an expanded detail end view of the distal segment of the vessel lumen probe of FIG. 9;

FIG. 14 is a side view in partial cross-section of a sixth embodiment of a vessel surface probe that can be percutaneously employed in conjunction with a sixth embodiment of a vessel lumen probe traversing an arterial occlusion to ascertain the boundaries of the obstruction by light emission by a photo emitter of the vessel surface probe and light detection by a photosensor of the vessel lumen probe;

FIG. 15 is an expanded detail side view of the distal segment of the vessel lumen probe of FIG. 14;

FIG. 17 is a side view in partial cross-section of the vessel surface probe incorporating a marker of FIG. 16 in preparation for marking a determined site of the arterial wall; and FIG. 18 is a side view in partial cross-section of the vessel surface probe incorporating a marker of FIG. 16 marking a determined site of the arterial wall.

DETAILED DESCRIPTION OF THE PREFERRED EMBODIMENTS

In the following detailed description, references are made to illustrative embodiments for carrying out the invention. It is understood that other embodiments can be utilized without departing from the scope of the invention.

For example, while a preferred method of performing a coronary artery anastomosis in a thoracoscopic CABG procedure will be described below, it is to be understood that the principles of the present invention can be applied to a wide variety of surgical procedures, both conventional, open procedures, as well as minimally invasive procedures. The present invention is also of great use to facilitate other medical procedures where it is desirable to locate the distal end of a catheter or guidewire or the like within a lumen of a body vessel.

Figure 1:
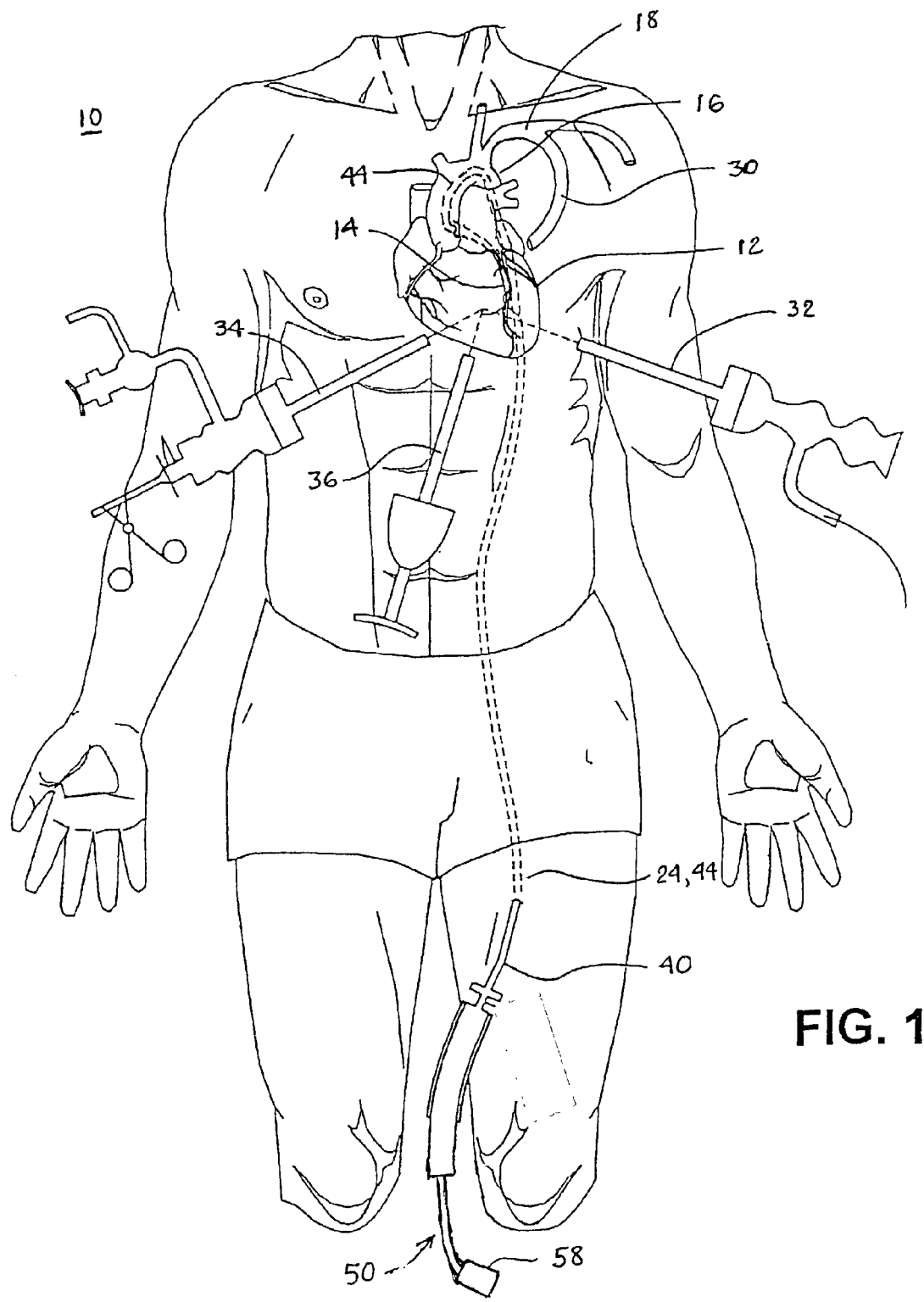
FIG. 1 is an illustration of the preparation of a patient for a percutaneous CABG procedure and particularly the determination of a suitable anastomosis site in a coronary artery.

The initial stages of an artery-to-artery coronary bypass procedure in accordance with the present invention in which an end-to-side vascular anastomosis is to be established between the severed end of the left internal mammary artery ("LIMA") 12 and the side-wall of the left anterior descending coronary artery ("LAD") 14 distally to the site of an obstruction is illustrated in FIG. 1. It will be understood that an angiography or other type of analysis of the coronary arteries of the heart of the patient 10 has been completed to identify the obstruction in the LAD coronary artery 14. Typically, the surgeon will already have an angiogram or some other analysis of the affected coronary artery available as a result of the earlier diagnosis of the necessity for the coronary bypass.

The patient 10 is placed under general anesthesia, and the patient's left lung is deflated using conventional techniques after placing a patient 10 under general anesthesia. The patient 10 is placed in a lateral decubitus position on his right side, and multiple small percutaneous incisions are made in the chest wall for receipt of surgical instruments. As used herein, the term "percutaneous" refers to any penetration through the skin of the patient, whether in the form of a small cut, incision, hole, cannula, trocar sleeve or port or the like,. For example, two small incisions are made in the chest wall of patient 10 at different intercostal positions, while a third incision is made just below the sternum.

First, the surgeon identifies a suitable position for insertion of a Beress insufflation needle or other suitable needle based upon the pathology and anatomy of the patient 10. Typically, this needle will be inserted between the fifth or sixth intercostal space along the anterior axillary line and into the region between the parietal pleura and the pericardium. The parietal pleura and pericardium are then separated, and the Beress needle is removed.

A first trocar (not shown) having a sharpened tip is inserted in the lumen of port 32 having a diameter of approximately 8 to 12 mm and, preferably, 10 mm, and the assembly is then inserted into the thoracic cavity along the same path traveled by the Beress insufflation needle. The trocar is then removed from port 32 and a conventional endoscopic telescope or thoracoscope (not shown) is introduced through the port 32 into the thoracic cavity. This thoracoscope is used to directly visualize the thoracic cavity and obtain a left lateral view of the pericardial sac or pericardium over the heart 30.

The surgeon determines the best locations for insertion of the assembly of a second trocar (not shown) and port 34 and the assembly of a third trocar (not shown) and port 36 based upon direct visualization through the thoracoscope of the pericardium overlying the heart 30, the presumed locations of the coronary artery of interest and the source artery as well as the anatomy and pathology of the patient 10 determined through, for example, biplane fluoroscopy and the previously conducted angiogram. Typically, the second trocar and port 34 is inserted through the intercostal wall and into the thoracic cavity, and the third trocar and port 36 is inserted through the subxyphoid space. Additional trocars or other instruments can be inserted percutaneously as necessary. Often, it will be advantageous to insert a fourth trocar and port for introducing a clipping or suturing device into the thoracic cavity. In each case, the trocars are removed leaving the ports in place. The parietal pleura is dissected and the pericardial sac is opened by instruments introduced through the second port 34 and/or the third port 36 using conventional techniques while visualizing the site through the thoracoscope. The thoracoscope is used to view the LAD coronary artery 14, in this case, to the extent that it can be seen because of overlying fatty tissue or its depth within the myocardium, and the location of the source artery, LIMA 12 in this case.

Figure 2:
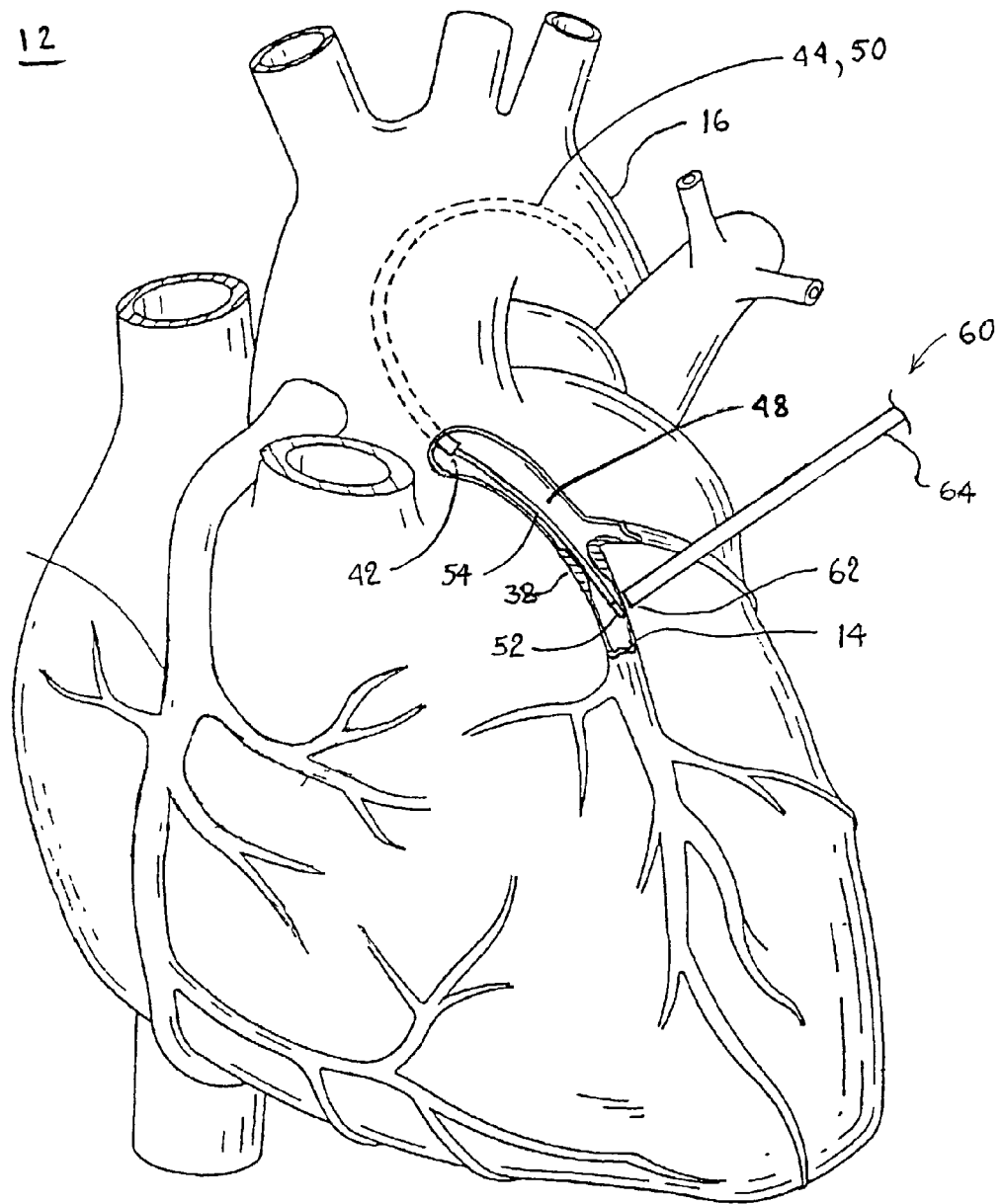
FIG. 2 is a schematic illustration of the heart and the use of a percutaneous, vessel surface probe in conjunction with a vessel lumen probe to ascertain the path of the coronary artery and the boundaries of an obstruction of the coronary artery.

At this juncture, the LAD coronary artery 14 is identified and the location of the occlusion 38 is ascertained employing the apparatus and methods of the present invention. As shown in FIGS. 1 and 2, the catheter body 44 of a femoral catheter 40 is introduced into the femoral artery 24 and advanced into the aorta 16 to locate the femoral catheter distal end 42 at or within the ostium of the LAD coronary artery 14. An elongated vessel lumen probe incorporating one of the vessel lumen probe elements of the present invention at the probe distal end 52 of the probe body 54 is advanced through the catheter lumen and out of the catheter lumen distal end opening into the LAD coronary artery 14. The lumen probe distal end 52 is then advanced, if possible, through the occlusion 38 to position the vessel lumen probe element downstream from the occlusion 38 by rotation and back and forth manipulation of the probe proximal end 58 exiting the femoral catheter 40. A radiopaque ring or the like is carried on the vessel lumen probe body 54 at or somewhat proximal to the vessel lumen probe distal end 52 so that advancement of the vessel lumen probe distal end 52 from the catheter lumen end opening and within the arterial lumen of the LAD coronary artery 14 can be monitored via fluoroscopy.

The progress of the vessel lumen probe distal end 52 as it is advanced through or is blocked by the occlusion 38 is also ascertained employing a vessel surface probe 60 that is advanced through one of the ports 34 and 36. The surface probe distal end 62 of the surface probe body 64 is applied against the epicardium over the suspected location of the LAD coronary artery 14 while the vessel surface probe 60 and the epicardial surface are observed through the thoracoscope inserted through port 32. The surface probe distal end 62 of the surface probe body 64 is moved about against the epicardium over the suspected location of the LAD coronary artery 14 until a surface probe element sensor of the present invention at the surface probe distal end 62 interacts with the lumen vessel element of the vessel lumen probe 50. The positioning of the surface probe distal end 62 over the epicardium adjacent to the vessel lumen probe distal end 52 within the lumen of LAD coronary artery 14 is shown schematically in FIG. 2. The surface probe distal end 62 can be perpendicular to or oriented at any convenient angle to axis of the surface probe body 64.

Figure 3:
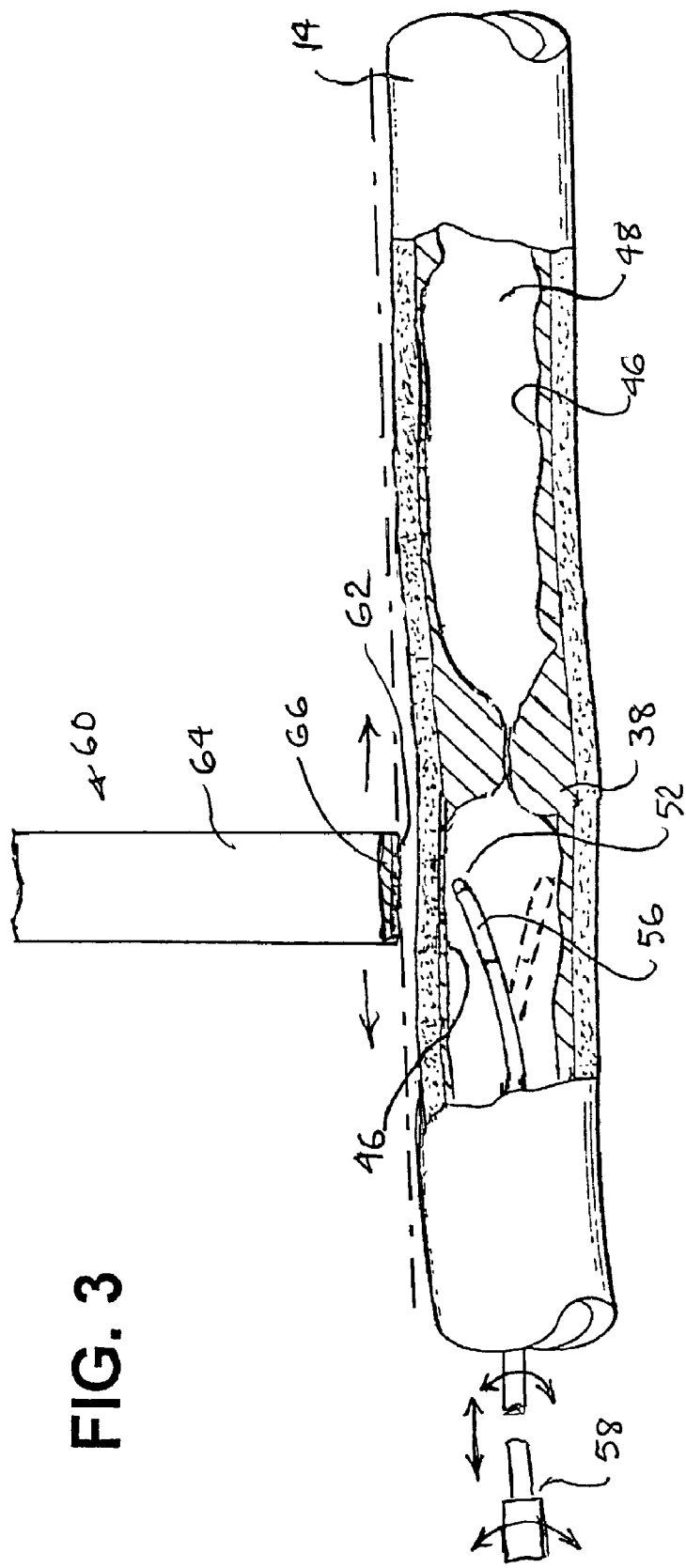
FIGS. 3-5 are side views in partial cross-section of the manipulation of the vessel surface probe against the epicardium overlying the artery of interest while a vessel lumen probe traverses the arterial lumen proximal to, within, and distal to an occlusion whereby the occluded and open segments of the arterial lumen can be ascertained as a function of the proximity of an arterial location identifying means of the vessel lumen probe and a probe location sensor of the vessel surface probe.
Figure 4:
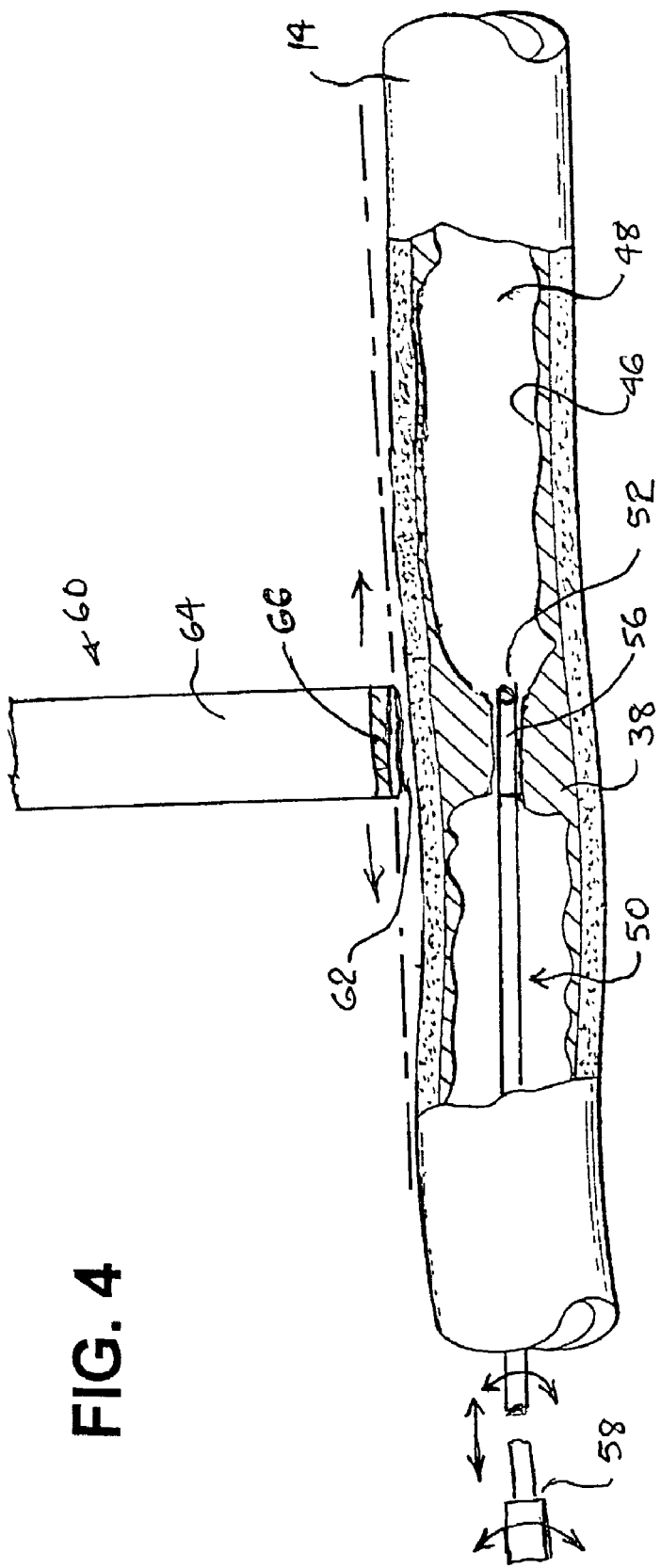
Figure 5:
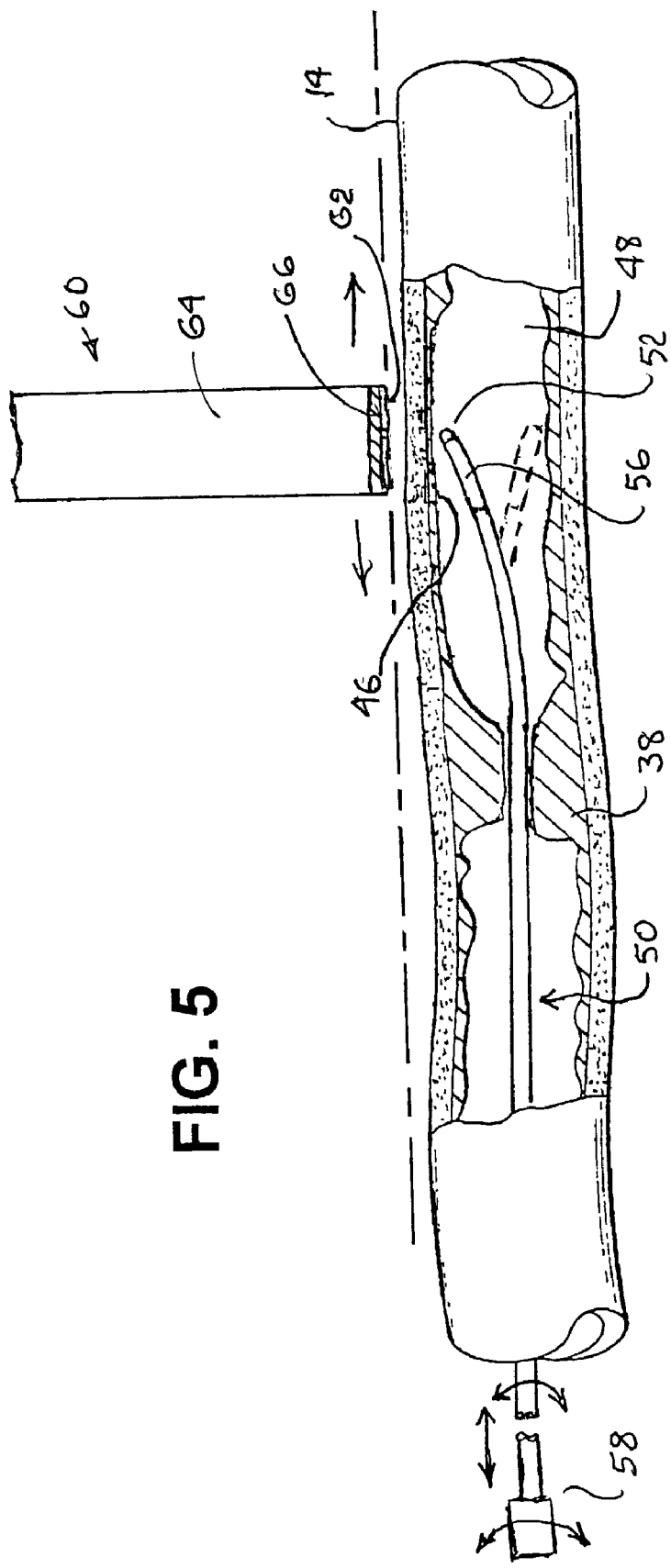

Turning to FIGS. 3-5, in accordance with the present invention, the vessel lumen probe distal end 52 within arterial lumen 48 is adapted to be rotated from the vessel lumen probe proximal end 58 (also shown in FIG. 1) or rotates under the influence of the surface probe element sensor 66. In this way, the lumen probe element 56 at or near the vessel lumen probe distal end 52 can be directed as close as possible toward the arterial wall 46 while the surface probe element sensor 66 of surface probe 60 is applied by and moved about the epicardial surface over the arterial wall 46 by the surgeon. A predetermined interaction between the lumen probe element 56 and the surface probe element sensor 66 is discerned when the lumen probe element 56 is minimally separated from the surface probe element sensor 66. The minimal separation is achieved when the lumen probe element 56 is located in an unobstructed region of the arterial lumen 48 and vessel lumen probe distal end 52 is rotated and/or attracted or advanced toward the epicardial surface as shown in solid lines in FIGS. 3 and 5.

Therefore, the vessel lumen probe 50 and the vessel surface probe 60 can be employed to map the epicardial surface as the vessel lumen probe distal end 52 is advanced through the unobstructed upstream portion of the LAD coronary artery 14 shown in FIG. 3, traverses the obstruction 38 shown in FIG. 4, and is advanced through the unobstructed downstream portion of the LAD coronary artery 14 shown in FIG. 5. The epicardial surface can be marked by a marker or clips introduced via instruments advanced through one of the percutaneous ports 34 and 36 so that the LAD coronary artery 14 can be exposed and proximal and/or distal arteriotomies can be made as described above. Following creation of an arteriotomy, an anastomosis may be created using one or more sutures, staples, rings, clips, sleeves, stents, couplers, sealants, glues, and/or adhesives or the anastomosis may be created using one or more laser welding techniques. In addition, a robot may be used during creation of the anastomosis.

Figure 6:
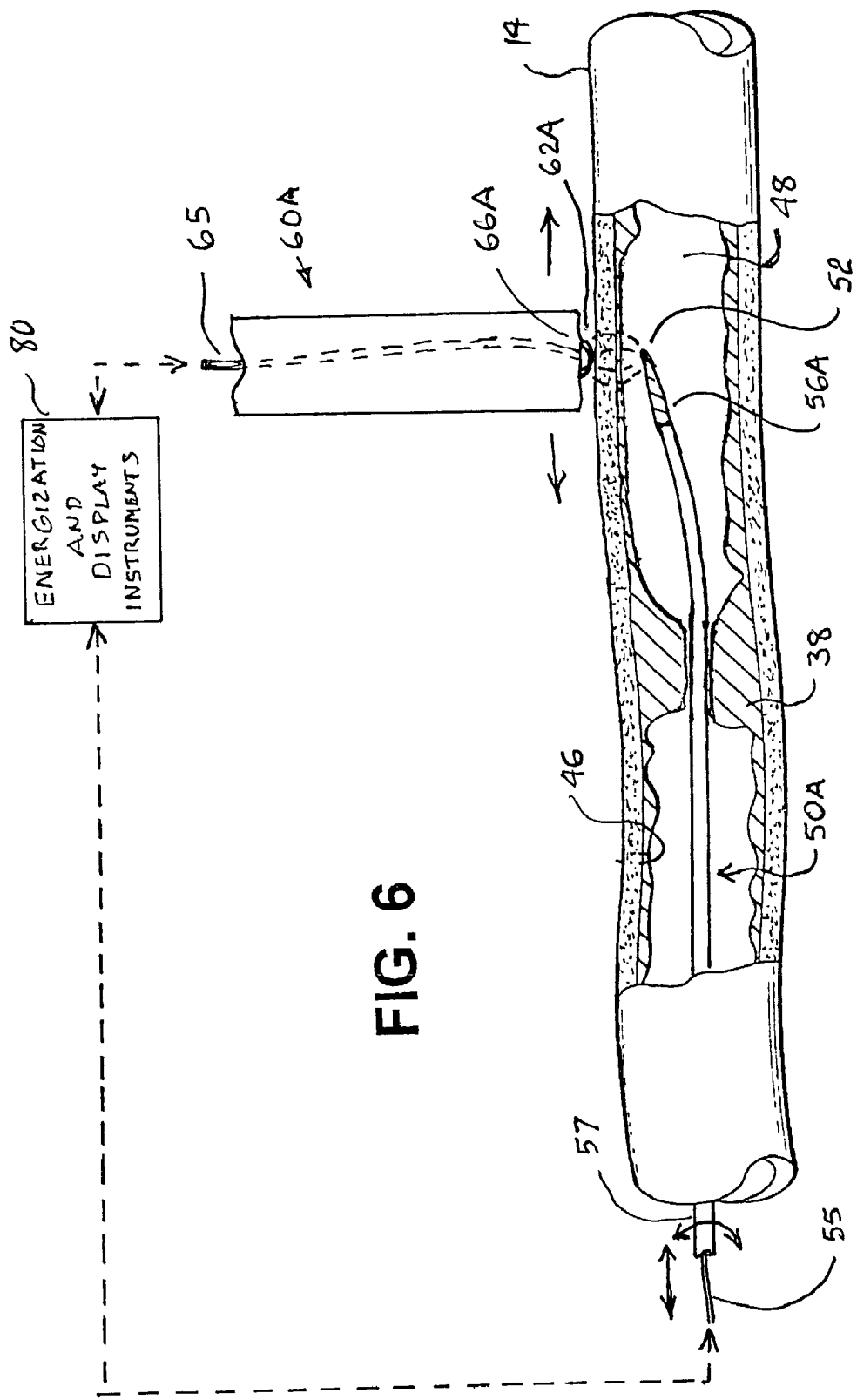
FIG. 6 is a side view in partial cross-section of a first embodiment of a vessel surface probe that can be percutaneously employed in conjunction with a first embodiment of a vessel lumen probe traversing an arterial occlusion to ascertain the boundaries of the obstruction by measurement of current flow between electrodes of the vessel surface probe and the vessel lumen probe.

In a first embodiment depicted in FIG. 6, the lumen probe element 56 comprises an exposed conductive electrode 56A, and the surface probe element sensor 66 comprises an exposed conductive electrode 66A. The electrode 56A is coupled through a conductor 55 within an insulating sheath 57 of vessel lumen probe 50A, and electrode 66A is coupled through a conductor 65 within the surface probe body 64, to external energization and display instruments 80 in the operating room. An electrical signal is developed having a magnitude that is proportional to the proximity of the electrodes 56A and 66A. The surgeon can observe a visual display of the signal on external instruments 80 and/or listen to audibly reproduced signal frequencies that vary as a function of the distance between the lumen probe electrode 56A and the surface probe electrode 66A. For example, a maximum or target amplitude or frequency of the electrical signal that is attained when the electrode 56A and the location surface probe electrode 66A are separated by a minimal distance.

In one variation, a low constant current is applied by instruments 80 between the wire electrode 56A and the location surface probe electrode 66A. The resulting voltage that varies as a function of the impedance between the electrodes 56A and 66A that is dictated by the intervening thickness of the arterial wall and any overlying tissue and obstructive plaque is measured by the instruments 80. Thus, the signal that is developed can be characterized as an impedance signal.

The vessel lumen probe distal end 52 is biased to extend toward the arterial wall when it is advanced from the femoral catheter lumen end opening unless it constrained by an occlusion 38 as shown in FIGS. 3-5. The vessel lumen probe distal end 52 and wire electrode 56A are rotatable as described above to sweep the wire electrode 56A around the arterial wall 46 within the arterial lumen 48 until the derived impedance signal indicates that the wire electrode 56A is closest to the surface probe electrode 66A. After it is determined that the relative locations of the two electrodes are optimized, RF energy can be applied between the two electrodes, the vessel probe electrode and the surface probe electrode, at an energy level and for a duration sufficient to form an opening via cauterization through the vessel wall, thus forming an arteriotomy. The applied RF energy heats and explodes the tissue cells contacted by the electrodes thereby forming an opening, or arteriotomy, through the arterial wall. The length, width and shape of the arteriotomy will depend upon the corresponding length, width and shape of the two electrodes. Following the formation of the arteriotomy, a graft, as described above, can be attached to the opening in a manner that prevents leakage of blood. The attaching step can comprise the use of one or more anastomotic devices, e.g., a suture, a staple, a ring, a clip, a sleeve, a stent, or a coupler. In addition, the attaching step can comprise the use of one or more anastomotic agents, e.g., a sealant, a glue, or an adhesive, or the use of a robot or laser.

Figures 7, 8:
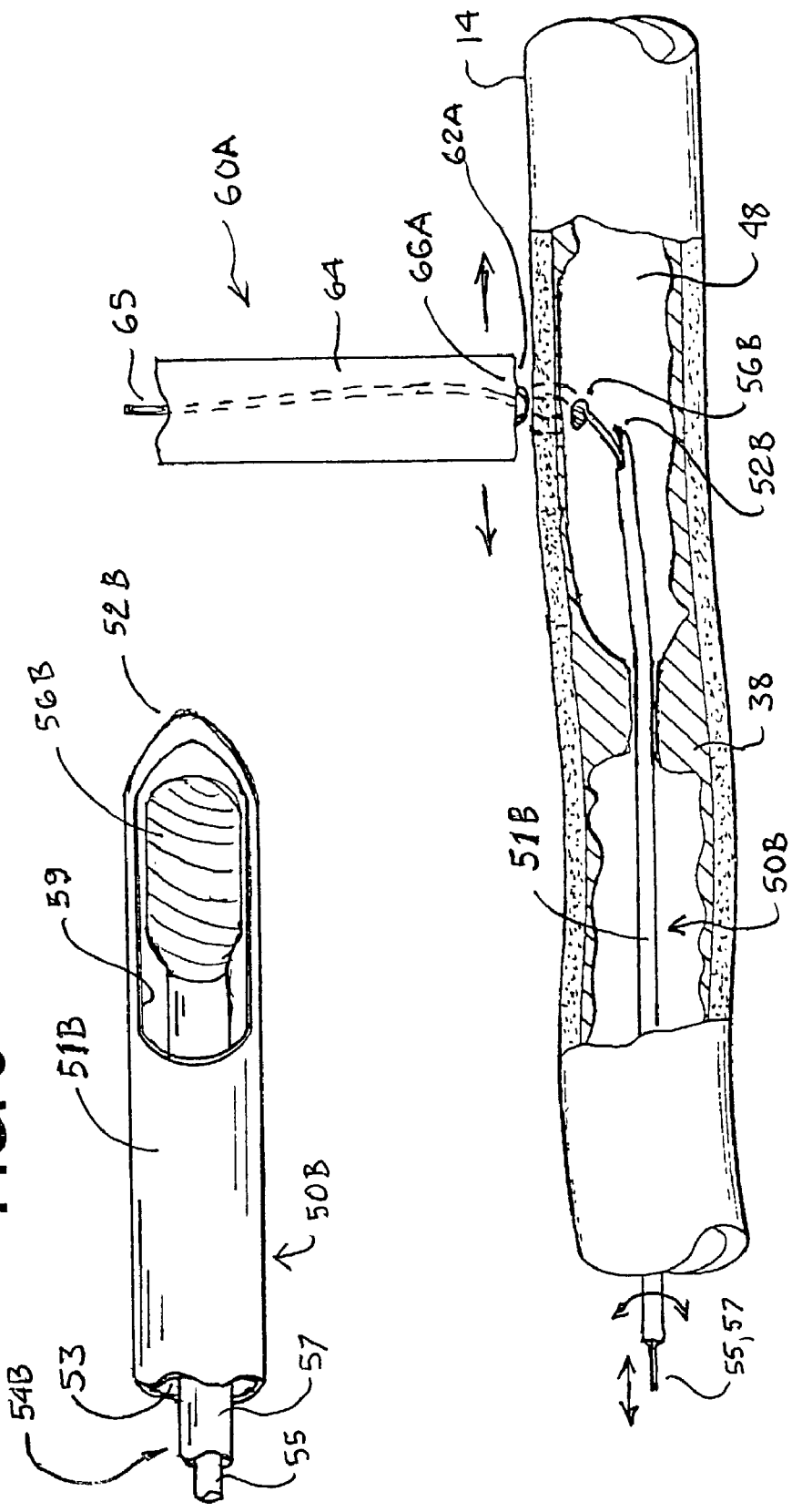
FIG. 7 is a side view in partial cross-section of a second embodiment of a vessel surface probe that can be percutaneously employed in conjunction with a second embodiment of a vessel lumen probe traversing an arterial occlusion to ascertain the boundaries of the obstruction by measurement of current flow between electrodes of the vessel surface probe and the vessel lumen probe.
FIG. 8 is an expanded detail view of the distal segment of the vessel lumen probe of FIG. 7.

In a variation of the first embodiment depicted in FIGS. 7 and 8, the vessel lumen probe 50B comprises a coaxially nested elongated flexible vessel lumen probe sheath 51B and probe wire 54B. The probe sheath 51B has a sheath lumen 53 terminating in a side lumen opening 59 adjacent to the vessel lumen probe distal end 52B. The probe wire 54B comprise a conductor 55 insulated with an insulating layer 57 and extending between a distal conductive electrode 56B and a proximal connector element (not shown) adapted to be connected to external instrumentation. The probe wire 54B extends through the lumen 53 of the probe sheath 51B. The conductive electrode 56B can be retracted into or against the opening 59 or advanced outward by manipulation of the proximal end (not shown) of the probe wire 54B as shown in FIG. 7. The conductors 55 and 65 are coupled to the external energization and display instruments 80 of FIG. 6, and the vessel lumen probe 50B and vessel surface probe 60A are employed in the same manner as described above with respect to FIG. 6.

In variations of a further embodiment depicted in FIGS. 9-12, magnetic field attraction is employed to draw a magnetic field responsive element or magnet at the distal end of the vessel lumen probe toward a magnetic surface probe element sensor supported by the surface probe. The surgeon can feel the increased strength of the magnetic field force through the body of the surface probe when the magnetic surface probe element sensor is strongly attracted toward the arterial wall by the magnetic field responsive element and the reduced strength of the magnetic field force when the surface probe element sensor is separated from the arterial wall by the obstruction 38.

In the variation depicted in FIG. 9, the surface probe element sensor is a permanent magnet 66C supported at the surface probe end 62C of the surface probe 60C. The vessel lumen probe 50C comprises an elongated flexible shaft or probe body 57C supporting a further magnet or magnetic field responsive element 56C that is drawn toward the arterial wall 46 by the magnetic field of the surface probe magnet 66C as the location surface probe distal end 62C is moved over the epicardial surface and the probe body 57C is rotated to sweep the magnet or magnetic field responsive element 56C around the arterial wall 46. The vessel lumen probe distal end 52C can be biased to extend toward the arterial wall 46 when it is advanced from the femoral catheter lumen end opening unless it constrained by an occlusion 38 as shown in FIGS. 3-5.

In certain procedures, it would be desirable to be able to direct a further tool, guidewire, or the like (collectively referred to as a wire herein) introduced into the vessel lumen into or through the vessel wall at the point where the surface probe sensor locates the lumen probe element. The wire distal end can be employed for a variety of purposes, e.g., to introduce other devices over the wire through the vessel wall at the site. Or, it would be desirable to introduce drugs, cells, genes or other materials, e.g., anastomotic materials, to the vessel or into the vessel wall at the point where the surface probe sensor locates the lumen probe element.

Thus, in a variation depicted in FIGS. 10 and 11, the magnet or magnetic field responsive element 56C is located on one side of the vessel lumen probe distal end 52C. A rotatable joint 78 is formed in the probe body 57C proximal to the magnet or magnetic field responsive element 56C. The probe body 57C is thereby formed of a probe body proximal section joined to a probe body distal section by the rotatable joint 78 enabling rotation of the probe body distal section with respect to the probe body proximal section. The distal end 52C and the magnet or magnetic field responsive element 56C can therefore rotate into alignment with the externally applied magnetic field of the surface probe magnet 66C as shown in FIG. 9.

In addition, a probe lumen 70 extends the length of the vessel lumen probe 50C through the rotatable joint 78 and to a lumen port 75 that is disposed through or aligned with the magnet or magnetic field responsive element 56C. A wire 84 can be extended through the probe lumen 70 after it is determined that the distal end 52C and the magnet or magnetic field responsive element 56C are rotated into alignment with the externally applied magnetic field of the surface probe magnet 66C as shown in FIG. 9. The wire distal end 86 can be extended out of the port 75 as shown in FIGS. 9 and 10.

The wire distal end 86 can be extended from the vessel wall, grasped with an instrument, and pulled outward through a port or incision, if so desired. The vessel lumen probe 50C can then be withdrawn from the vessel lumen 48 and the femoral catheter 40 leaving the wire 84 in place. Further dilators or catheters or arteriotomy tools can be introduced over the wire into the vessel lumen 48. In addition, the wire can be used to guide or place an anastomotic delivery tool or an anastomotic device into position. For example, the wire can be placed within a lumen of the anastomotic delivery tool or the lumen of the anastomotic device, e.g., a coupler, a sleeve, a stent or a ring. The anastomotic device or delivery tool can then be guided along the wire to the vessel wall and/or vessel lumen.

Figure 12:
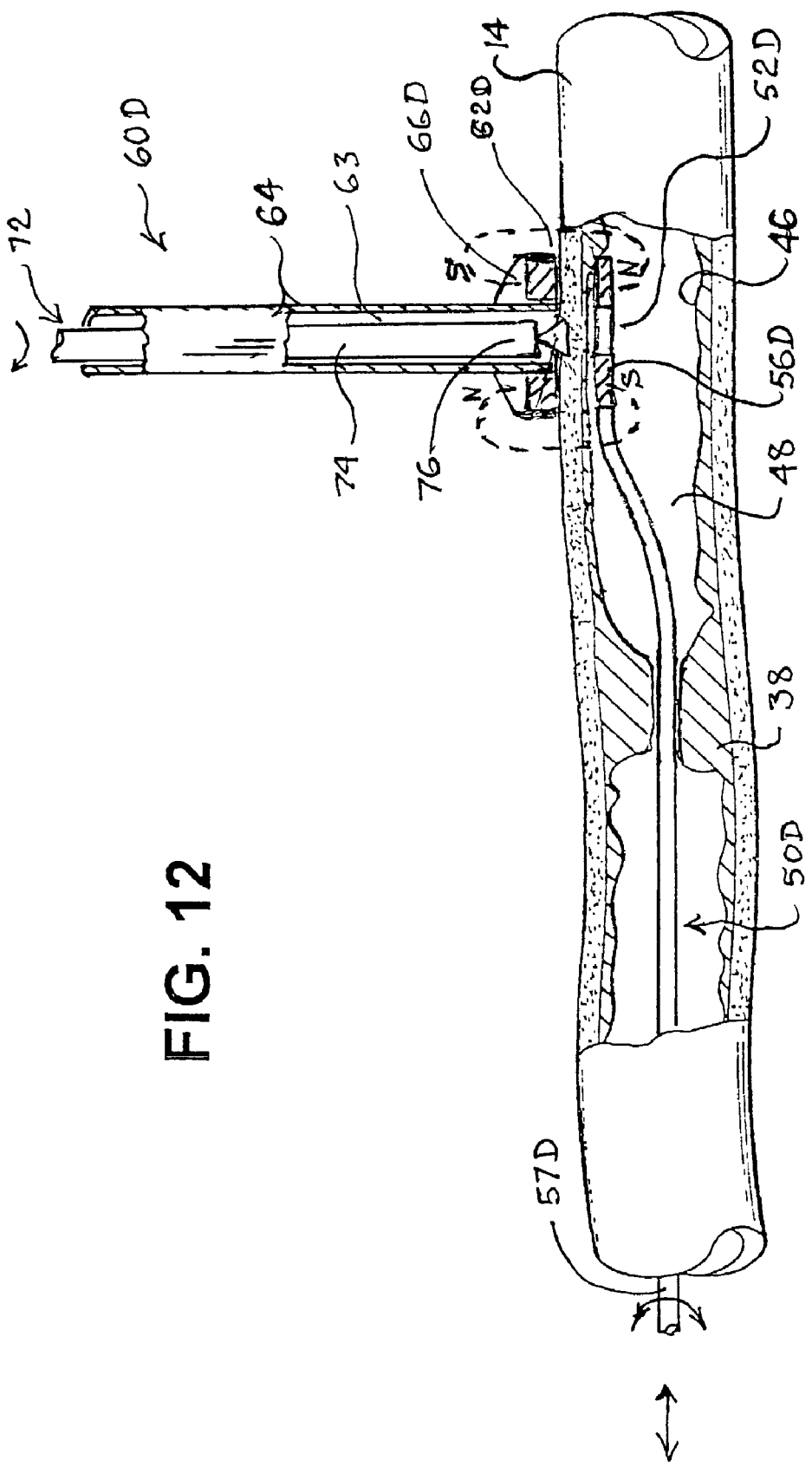
FIG. 12 is a side view in partial cross-section of a fourth embodiment of a vessel surface probe that can be percutaneously employed in conjunction with a fourth embodiment of a vessel lumen probe traversing an arterial occlusion to ascertain the boundaries of the obstruction by magnetic field attraction between magnets of the vessel surface probe and the vessel lumen probe.

A still further variation of the embodiment employing magnetic field attraction between a magnet 56D at the distal end 52D of the vessel lumen probe 50D and a magnet 66D mounted to a surface probe distal end 62D of location surface probe 60D is illustrated in FIG. 12. The vessel lumen probe 50D is introduced through the femoral catheter 40 of FIG. 1, and the elongated vessel lumen probe body 57D is depicted in FIG. 12 extending through the vessel lumen 48 and occlusion 38. The magnet or magnetic field responsive element 56D preferably comprises a pair of oppositely poled magnets. The vessel surface probe 60D preferably comprises a pair magnets or a segmented ring magnet 66D mounted to the surface probe distal end 62D that is moved over the epicardium to draw the magnets of magnetic field responsive element 56D toward it as described above with respect to the embodiment of FIG. 9. In this embodiment, the surface probe 60D has a surface probe lumen 63 that a further instrument 72 can be advanced so as to make contact with or extend through the arterial wall 46 at the site where an arteriotomy is to be made. For example, an arteriotomy cutting blade 76 can be advanced through the lumen 63 of the location surface probe 60D to make a cut into the vessel wall. Or, a puncture can be made through the vessel wall to enable introduction of a guidewire or the like through the lumen 63 of the location surface probe 60D and into the vessel lumen 48. Or, a marker of the type described further herein can be introduced through the lumen 63 of the location surface probe 60D to mark the site that is identified.

In one embodiment of the present invention, magnetic field repulsion between a magnet of a vessel lumen probe and a magnet of a surface probe can be used to introduce an instrument, e.g., a guidewire, into an interior chamber of an organ, e.g., the heart, from an organ vessel lumen, e.g., a coronary artery lumen. The vessel surface probe can, for example, comprise an oppositely poled magnet or magnets as compared to the vessel lumen probe so that when the surface probe distal end is moved over the epicardium, the vessel lumen probe is repelled or moved toward the opposite wall of the vessel. In this embodiment, the vessel lumen probe has a lumen that a further instrument can be advanced so as to make contact with or extend through the arterial wall towards the interior of the heart. For example, a guidewire can be directed by the surface probe to puncture through the vessel wall, through the wall or myocardium of the heart, and into an interior chamber of the heart, e.g., the left ventricle. The guidewire can then be used, for example, to introduce and/or place a stent or shunt in the wall of the heart, thereby allowing blood to flow from the interior chamber of the heart and into the coronary vessel. For example, the stent can be placed so that it extends between the left ventricle and a coronary artery. The stent would allow blood to flow from the left ventricle into the coronary artery during diastole. In another embodiment of the present invention, magnetic field attraction between a magnet of a vessel lumen probe and a magnet of a surface probe can be used to introduce an instrument, e.g., a guidewire, into an organ, e.g., the heart, from an organ vessel, e.g., a coronary artery. In this embodiment, the vessel surface probe can be placed within an interior chamber of the organ, e.g., the left ventricle of the heart. When the surface probe distal end is moved within the interior chamber, the vessel lumen probe is drawn toward the wall of the vessel closes in proximity to the interior chamber of the heart. Again, the vessel lumen probe has a lumen that a further instrument can be advanced so as to make contact with or extend through the arterial wall towards the interior of the heart. A guidewire can be passed through the wall of the vessel, through the wall of the heart and into an interior chamber of the heart.

Figure 13:
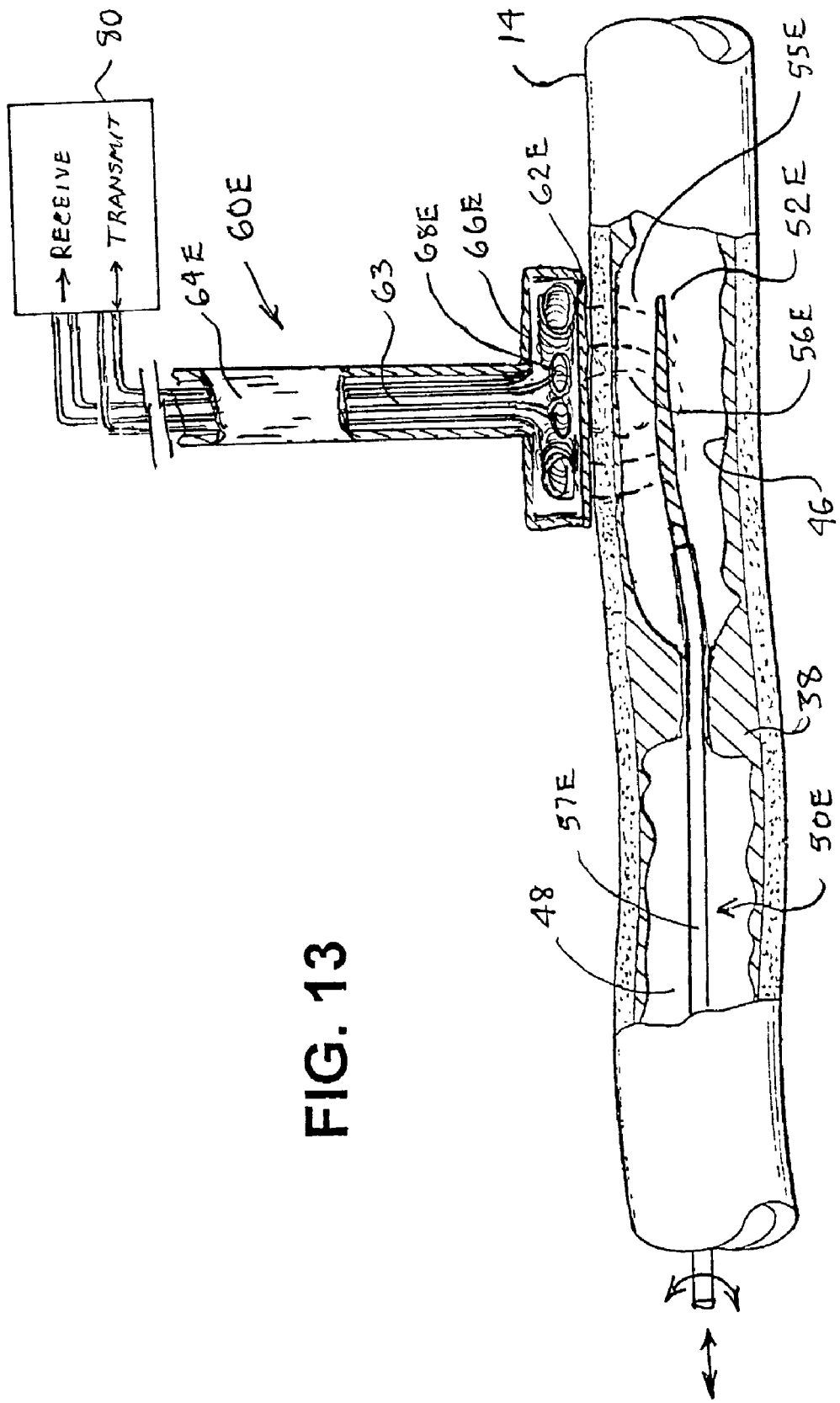
FIG. 13 is a side view in partial cross-section of a fifth embodiment of a vessel surface probe that can be percutaneously employed in conjunction with a fifth embodiment of a vessel lumen probe traversing an arterial occlusion to ascertain the boundaries of the obstruction by metal detection techniques.

In a still further variation of the embodiment employing magnetic field detection, it would be possible to employ a magnetic field sensor in substitution for the one of the magnets 56D and 66D. A MAGFET integrated circuit or a MEMS device responsive to a magnetic field incorporated into an integrated circuit and providing or altering an electrical signal that depends in magnitude or frequency or phase shift or the like on the strength of the magnetic field could be employed as such a magnetic field sensor. In a still further variation depicted in FIG. 13, the surface probe element sensor of surface probe 60E comprises a metal detection surface probe element sensor 66E mounted at the distal end of surface probe body 64E. The vessel lumen probe distal end 52E of vessel lumen probe 50E supports a lumen probe element comprising a dense metal material coil or rod 56C. The metal detector head at the distal end of the surface probe body 64E encloses or supports an outer transmitter coil 62E and an inner receiver coil 68E that are coupled to an externally disposed conventional metal detector transceiver 80 through conductors extending through the surface probe body 64E. The metal detector transceiver generates an AC signal, e.g., a 6.6 KHz signal that is applied through a conductor to the transmitter coil 62E. The oscillating magnetic field 55E produced by the transmitter coil 62E extends orthogonally to the coil loop plane a distance through the lumen of the vessel, in this case lumen 48 of the LAD coronary artery 14. The receiver coil 68E is directionally shielded from the generated magnetic field 55E. The generated magnetic field 55E induces an eddy current in any conductive object that is within the generated magnetic field 55E, in this case the conductive vessel lumen probe distal end 52E, causing the conductive object to generate a weak induced magnetic field 56E that can intercept the receiver coil 68E and induce a current in receiver coil 68E. The strength of the induced current depends on the size and material of the conductive object and its distance from the receiver coil 68E. The induced current is conducted to receiver electronics in the metal detector transceiver 80. The metal detector transceiver 80 develops an audible and/or visual display that indicates the distance between the conductive object and the receiver coil The vessel lumen probe distal end 52E is biased to extend toward the arterial wall 46 when it is advanced from the femoral catheter lumen end opening unless distal end 52E is constrained by an occlusion as shown in FIG. 4. Again, the vessel lumen probe distal end 52E and metallic lumen probe element are rotatable to sweep the metallic coil or rod probe element 56C around the arterial wall 46 within the arterial lumen 48 while the signal intensity or frequency developed by the metal detection sensor 66E is monitored to locate the vessel lumen probe distal end 52.

The metal detection surface probe element sensor 66E of surface probe body 64E can be used to find metal objects, e.g., guidewires, stents, surgical clips and/or staples, within a body vessel lumen or wall.

In a still further embodiment depicted in FIGS. 14 and 15, the vessel lumen probe 50F comprises a light emitter, e.g. a light conducting fiber or pipe 57F, that is movable axially within a light pipe sheath lumen 53F of a light pipe sheath 51F having a distal sheath opening 59F. The light pipe 57F and light pipe sheath 51F are advanced through the femoral catheter lumen and into the arterial lumen 48 of LAD coronary artery 14. The light pipe 57F can be axially moved out of the distal sheath opening 59F so that the light emitted from the light pipe distal end 56F is selectively directed toward the arterial wall 46 unless constrained by an occlusion 38 as shown in FIGS. 3-5. The light pipe 57F and light pipe sheath 51F can be rotated to sweep the emitted light about the arterial lumen 48 so that the light can be directed outward through the arterial wall 46 and the overlying epicardial and fatty tissues that can be obscuring the LAD coronary artery 14 from view.

The depicted vessel surface probe 60F can be employed to detect the emitted light transmitted through the arterial wall 46 toward the epicardium and tissues that can be obscuring the LAD coronary artery 14. The surface probe element sensor of the vessel surface probe 60F comprises a photosensor 66F that develops or modulates an electrical signal proportional to the intensity of light emitted by the light pipe distal end 56F that strikes the photosensor 66F. The light pipe distal end 56F is aimed outward from the light pipe sheath distal opening 59F by manipulation of the proximal end portions of the light pipe sheath 51F and the light pipe 57F. The emitted light that is directed toward and impinges upon the photosensor 66F has a magnitude that is proportional to the density of tissue and any plaque between the photosensor 66F and the light pipe distal end 56F. An optical color filter selected to pass only light frequencies characteristic of light passed through tissue layers can be placed over the photosensor 66F to filter out ambient light. The surgeon can observe a visual display of the signal and/or listen to audibly reproduced signal frequencies that vary as a function of the light intensity. For example, a maximum or target amplitude or frequency of the electrical signal that is attained when the photosensor 66F and the light pipe distal end 56F are aligned and the vessel lumen 48 is minimally obstructed by plaque.

The epicardium can be directly observed by the surgeon employing the thoracoscope as shown in FIG. 1, and in cases it may be possible for the physician to observe the emitted light direction and intensity within unobstructed portions of the LAD coronary artery 14 and view the boundaries of the occlusion 38 when the light intensity is attenuated as the light pipe 57F and light pipe sheath 51F are directed through the occlusion 38 as shown in FIGS. 3-5.

The LAD coronary artery 14 is identified following one of the above-described procedures, and the overlying fatty tissue is dissected away to prepare the proximal and/or distal arterial sites for arteriotomy and anastomosis in any of the ways described in the various patents cited above and in clinical use. For example, the LIMA 12 is dissected, severed to provide a source vessel and shaped in preparation for the anastomosis procedure. An arteriotomy is made in the LAD coronary artery 14 downstream of the obstruction 38, and the prepared free end of the LIMA 12 is anastomosed to the LAD coronary artery 14 at the site of the arteriotomy.

Figure 16:
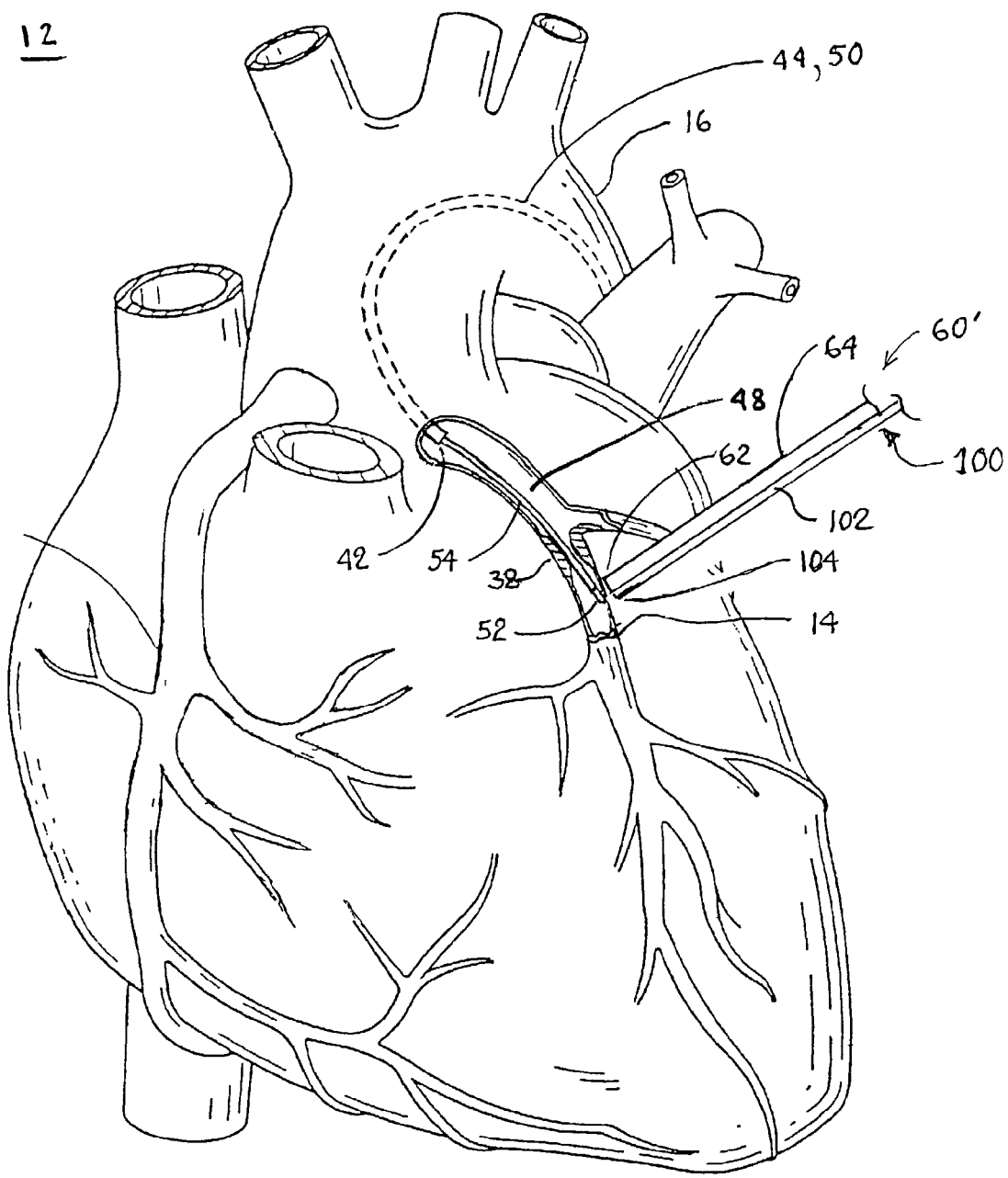
FIG. 16 is a schematic illustration of the heart and the use of a percutaneous, vessel surface probe incorporating an integral marker in conjunction with a vessel lumen probe to ascertain the boundaries of an obstruction of the coronary artery and mark a determined site of the arterial wall.

A further aspect of the present invention enabling the marking of a site of a vessel wall determined in accordance with the present invention is depicted in FIGS. 16-18. Any of the above-described vessel surface probes can be modified to incorporate such a marker that can be manipulated to dispense a marking ink or fluid onto the blood vessel after the site has been determined in any of the above-described ways or equivalent ways.

Thus, a surgical marker 100 is incorporated into the vessel surface probe 60 representing any such surface probe. The surgical marker comprises a tube 102 that can be formed integrally as part of or attached to the surface probe body 64 extending from the proximal end of the surface probe body 64 to an ink ejection port 104. The tube 102 is filled with non-toxic ink 110, such as methylene blue.

The nontoxic ink 110 is maintained within the tube by a flap valve 108. A bolus of the nontoxic ink 110 is selectively ejected from the ink ejection port 104 when a plunger 106 is depressed from the position depicted in FIG. 17 to the position depicted in FIG. 18 and the applied force opens the flap valve 108.

CONCLUSION

All patents and publications referenced herein are hereby incorporated by reference in their entireties.

It will be understood that certain of the above-described structures, functions and operations of the above-described preferred embodiments are not necessary to practice the present invention and are included in the description simply for completeness of an exemplary embodiment or embodiments. It will also be understood that there can be other structures, functions and operations ancillary to the typical CABG procedures that are not disclosed and are not necessary to the practice of the present invention.

In addition, it will be understood that specifically described structures, functions and operations set forth in the above-referenced patents can be practiced in conjunction with the present invention, but they are not essential to its practice.

It is therefore to be understood, that within the scope of the appended claims, the invention can be practiced otherwise than as specifically described without actually departing from the spirit and scope of the present invention.

We claim:

1. A method of identifying an obstruction in and a course of a body vessel of a patient that is hidden from direct view in a surgical field by body tissue overlying a vessel wall of the body vessel surrounding a vessel lumen of the body vessel comprising:
   surgically exposing through an incision at least a portion of body tissue overlying the vessel wall;
   introducing a vessel lumen probe having a lumen probe element at or near a vessel lumen probe distal end into the vessel lumen;
   introducing a surface probe element sensor of a vessel surface probe into the patient through the incision; and
   applying the surface probe element sensor of the vessel surface probe over the body tissue overlying the vessel wall, the surface probe element sensor adapted to provide a proximity indicating signal indicating the degree of proximity of the surface probe element sensor to the lumen probe element;
   determining the course of the body vessel relative to the body tissue overlying the vessel wall as a function of the relative strength of the signal when the surface probe element sensor is moved over the body tissue overlying the vessel wall relative to the lumen probe element positioned within the vessel lumen; and
   determining an obstruction within the body vessel as a function of the relative strength of the signal when the lumen probe element is moved within the vessel lumen.

2. The method of claim 1, further comprising the step of:
   sweeping the lumen probe element around the vessel wall within the vessel lumen while monitoring the indication of proximity.

3. The method of claim 1, wherein the lumen probe element comprises a metallic element and the surface probe element sensor comprises a metal detector coil assembly, and the applying step further comprises:
   energizing the metal detector coil assembly to develop a signal responsive to the detection of the metallic element through the vessel wall and body tissue overlying the vessel wall.

4. The method of claim 1, wherein the lumen probe element comprises a lumen probe magnet, and the surface probe element sensor comprises a magnet, the lumen probe magnet and surface probe element sensor arranged in polarity to enable magnetic attraction of the lumen probe element and lumen probe distal end toward the vessel wall in proximity to the surface probe element.

5. The method of claim 1, wherein the vessel lumen probe comprises a probe body having a probe lumen extending the length of the probe body to a distal lumen opening, the lumen probe element comprises a lumen probe magnet, and the surface probe element sensor comprises a magnet, the lumen probe magnet and surface probe element sensor arranged in polarity to enable magnetic attraction of the lumen probe magnet and lumen probe distal end toward the vessel wall in proximity to the surface probe element sensor and further comprising the step of:

introducing a guidewire through the probe lumen to exit the distal lumen opening and perforate through the body vessel wall when the lumen probe distal end is magnetically attracted toward the vessel wall.

6. The method of claim 1, wherein the lumen probe element comprises a magnet, and the surface probe element sensor comprises a magnet, whereby magnetic attraction or repulsion force between the magnets provides the proximity indicating signal.

7. The method of claim 1, wherein the lumen probe element comprises an electrically conductive, vessel probe electrode, and the surface probe element sensor comprises an electrically conductive, surface probe electrode, and the applying step further comprises:

applying electrical energy between the electrically conductive, vessel probe electrode and the electrically conductive, surface probe electrode; and measuring the impedance between the between the electrically conductive, vessel probe electrode and the electrically conductive, surface probe electrode to develop an impedance signal related to the proximity of the electrically conductive, vessel probe electrode to the electrically conductive, surface probe electrode.

8. The method of claim 7, further comprising the step of:
applying RF energy between the vessel probe electrode and the surface probe electrode at an energy level and for a duration sufficient to form an opening through the vessel wall.

9. The method of claim 8, further comprising the step of:
attaching a graft at the opening in a manner that prevents leakage of blood.

10. The method of claim 9, wherein the graft is a free graft.

11. The method of claim 9, wherein the graft is an attached graft.

12. The method of claim 9, wherein the attaching step further comprises the use of one or more anastomotic devices selected from the group comprising a suture, a staple, a ring, a clip, a sleeve, a stent and a coupler.

13. The method of claim 9, wherein the attaching step further comprises the use of one or more anastomotic agents selected from the group comprising a sealant, a glue and an adhesive.

14. The method of claim 9, wherein the attaching step further comprises the use of a robot.

15. The method of claim 9, wherein the attaching step further comprises the use of a laser.

16. The method of claim 1, wherein the vessel lumen probe comprises a probe sheath having a sheath lumen extending the length of the vessel lumen probe to a distal lumen opening, and a probe wire extending through the sheath lumen having an electrically conductive, vessel probe electrode, and the surface probe element sensor comprises an electrically conductive, surface probe electrode, and wherein:

the introducing step further comprises:
advancing the probe sheath and probe wire into the vessel lumen; and
manipulating the probe wire to extend the vessel probe electrode toward the vessel wall; and the applying step further comprises:

applying electrical energy between the electrically conductive, vessel probe electrode and the electrically conductive, surface probe electrode; and measuring the impedance between the between the electrically conductive, vessel probe electrode and the electrically conductive, surface probe electrode to develop an impedance signal related to the proximity of the electrically conductive, vessel probe electrode to the electrically conductive, surface probe electrode.

17. The method of claim 1, wherein the vessel lumen probe comprises a light transmitting and emitting light pipe having a light pipe proximal end adapted to be coupled to a light source and a light pipe distal end operable as the lumen probe element from which light source light is emitted, and the surface probe element sensor comprises a photosensor that responds to the frequency of light emitted by the light emitter and transmitted through the vessel wall and body tissue overlying the vessel wall.

18. The method of claim 1, wherein the vessel lumen probe comprises a light transmitting and emitting light pipe having a light pipe proximal end adapted to be coupled to a light source and a light pipe distal end operable as the lumen probe element from which light source light is emitted, the light pipe extending through the lumen of a light pipe sheath, and the surface probe element sensor comprises a photosensor that responds to the frequency of light emitted from the light pipe distal end and transmitted through the vessel wall and body tissue overlying the vessel wall, and wherein:

the introducing step comprises:
advancing the light pipe sheath and light transmitting and emitting pipe into the vessel lumen;
advancing the light transmitting and emitting light pipe out of the sheath lumen to dispose the light pipe distal end toward the vessel wall; and
transmitting light through the light pipe;

the applying step comprises applying the surface probe over the body tissue overlying the vessel wall so that the photosensor provides a proximity indicating signal indicating the degree of proximity of the photosensor to the light pipe distal end, whereby the location of the vessel lumen is determinable as a function of the relative strength of the signal.

19. The method of claim 18, further comprising the step of:
transmitting laser light energy through the light pipe at an energy level and for a duration sufficient to form an opening through the vessel wall.

20. The method of claim 19, further comprising the step of:
attaching a graft at the opening in a manner that prevents leakage of blood.

21. The method of claim 20, wherein the graft is a free graft.

22. The method of claim 20, wherein the graft is an attached graft.

23. The method of claim 20, wherein the attaching step further comprises the use of one or more anastomotic devices selected from the group comprising a suture, a staple, a ring, a clip, a sleeve, a stent and a coupler.

24. The method of claim 20, wherein the attaching step further comprises the use of one or more anastomotic agents selected from the group comprising a sealant, a glue and an adhesive.

25. The method of claim 20, wherein the attaching step further comprises the use of a robot.

26. The method of claim 1, further comprising the step of:
forming an opening through the vessel wall.

27. The method of claim 26, further comprising the step of: attaching a graft at the opening in a manner that prevents leakage of blood.

28. The method of claim 26, further comprising the step of: passing a guidewire through the opening.

29. The method of claim 28, further comprising the step of: passing the guidewire into an interior chamber of an organ.

30. The method of claim 29, wherein the organ is a heart.

31. The method of claim 28, further comprising the step of: passing the guidewire through an intercostal space.

32. The method of claim 1, further comprising the step of: harvesting the body vessel.

33. The method of claim 32, wherein the harvested body vessel is used in a CABG procedure.

34. The method of claim 1, further comprising the step of: avoiding the body vessel during a medical procedure.

35. The method of claim 34, wherein the medical procedure is selected from the group comprising cell delivery, gene delivery, drug delivery, lead delivery, and tissue ablation.

36. The method of claim 1, further comprising the steps of: applying a marker to the determined location; and marking the body tissue overlying the vessel wall at the determined location with the marker.

37. The method of claim 1, further comprising the steps of: applying a marker containing marking ink to the determined location; and dispensing marking ink from the marker onto the body tissue overlying the vessel wall at the determined location.

38. The method of claim 1, wherein:
the step of obtaining surgical access comprises obtaining surgical access to the epicardium of the heart of the patient;
the introducing step comprises introducing the vessel lumen probe having a lumen probe element at or near a vessel lumen probe distal end through the arterial system and into the arterial lumen of a coronary artery; and
the applying step comprises applying the surface probe element sensor over the tissue overlying the epicardium and arterial wall and moving the surface probe element to determine the path of the coronary artery and any obstruction of the coronary artery.

39. A system for identifying an obstruction in and a course of a body vessel in a patient that is hidden from direct view in a surgical field by body tissue overlying a vessel wall of the body vessel surrounding a vessel lumen of the body vessel comprising:
a vessel lumen probe having a lumen probe element at or near a vessel lumen probe distal end adapted to be introduced into the vessel lumen, wherein the lumen probe element is adapted to be positioned adjacent a luminal side of the vessel wall; and
a vessel surface probe having a surface probe element sensor at or near a vessel surface probe distal end adapted to be positioned through an incision in the patient and applied and moved about over the body tissue overlying the vessel wall, the surface probe element sensor adapted to provide a proximity indicating signal indicating the degree of proximity of the surface probe element sensor to the lumen probe element, wherein the course of the body vessel relative to the body tissue overlying the vessel wall is determinable as a function of the relative strength of the signal when the surface probe element sensor is moved over the body tissue overlying the vessel wall relative to the lumen probe element positioned within the vessel lumen, and wherein an obstruction within the body vessel is determinable as a function of the relative strength of the signal when the lumen probe element is moved within the vessel lumen.

40. The system of claim 39, wherein the vessel lumen probe further comprises means for sweeping the lumen probe element around the vessel wall within the vessel lumen while monitoring the indication of proximity.

41. The system of claim 39, wherein the lumen probe element comprises a metallic element and the surface probe element sensor comprises a metal detector coil assembly, and the applying step further comprises:
energizing the metal detector coil assembly to develop a signal responsive to the detection of the metallic element through the vessel wall and body tissue overlying the vessel wall.

42. The system of claim 39, wherein the lumen probe element comprises a lumen probe magnet, and the surface probe element sensor comprises a magnet, the lumen probe magnet and surface probe magnet selected in polarity to enable magnetic attraction of the lumen probe element and lumen probe distal end toward the vessel wall in proximity to the surface probe element.

43. The system of claim 39, wherein the vessel lumen probe comprises an elongated probe body having a probe body lumen extending the length of the probe body to a distal lumen opening, the lumen probe element comprises a lumen probe magnet, and the surface probe element sensor comprises a magnet, the lumen probe magnet and surface probe element sensor selected in polarity to enable magnetic attraction of the lumen probe magnet and lumen probe distal end toward the vessel wall in proximity to the surface probe magnet, the probe body lumen enabling introduction of a device or material to or into the interior vessel wall.

44. The system of claim 43, wherein the probe body is formed of a probe body proximal section joined to a probe body distal section by a joint enabling rotation of the probe body distal section with respect to the probe body proximal section, the lumen probe magnet is mounted to the probe body distal section along one side of the probe body distal section, and the probe lumen distal end opening is substantially aligned to the one side of the probe body distal section, whereby the probe body distal section is rotatable at the joint under the magnetic field attraction of the lumen probe magnet toward the surface probe magnet and the probe lumen distal end opening is directed toward the vessel wall that the one side of the probe body distal section faces.

45. The system of claim 44, further comprising an elongated wire extending between wire proximal and distal ends and sized to fit into and be advanced through the probe body lumen of the probe body proximal and distal sections to locate the wire distal end at or extending through the vessel wall.

46. The system of claim 39, wherein the lumen probe element comprises a magnet, and the surface probe element sensor comprises a magnet, whereby magnetic attraction or repulsion force between the magnets provides the proximity indicating signal.

47. The system of claim 39, wherein the lumen probe element comprises an electrically conductive, vessel probe electrode, and the surface probe element sensor comprises an electrically conductive, surface probe electrode, and further comprising:
means for applying electrical energy between the electrically conductive, vessel probe electrode and the electrically conductive, surface probe electrode; and
means for measuring the impedance between the electrically conductive, vessel probe electrode and the electrically conductive, surface probe electrode to develop an impedance signal related to the proximity of the electrically conductive, vessel probe electrode to the electrically conductive, surface probe electrode.

48. The system of claim 39, wherein:

the surface probe element sensor comprises an electrically conductive, surface probe electrode; and the vessel lumen probe comprises an elongated probe sheath enclosing a sheath lumen extending from a probe sheath proximal end to a distal lumen opening near a probe sheath distal end and an elongated probe wire sized to fit within the sheath lumen, the probe wire having an electrically conductive, vessel probe electrode adapted to move with respect to the distal lumen opening through manipulation of the probe wire to extend the vessel probe electrode toward the vessel wall;

and further comprising:

means for applying electrical energy between the electrically conductive, vessel probe electrode and the electrically conductive, surface probe electrode; and means for measuring the impedance between the electrically conductive, vessel probe electrode and the electrically conductive, surface probe electrode to develop an impedance signal related to the proximity of the electrically conductive, vessel probe electrode to the electrically conductive, surface probe electrode.

49. The system of claim 39, wherein:

the vessel lumen probe comprises an elongated light transmitting and emitting light pipe having a light pipe proximal end adapted to be coupled to a light source and a light pipe distal end from which light source light is emitted; and the surface probe element sensor comprises a photosensor that responds to the frequency of light emitted by the light emitter and transmitted through the vessel wall and body tissue overlying the vessel wall.

50. The system of claim 39, wherein:

the vessel lumen probe comprises:

an elongated probe sheath enclosing a sheath lumen extending from a probe sheath proximal end to a distal lumen opening near a probe sheath distal end; and an elongated light transmitting and emitting light pipe having a light pipe proximal end adapted to be coupled to a light source and a light pipe distal end from which light source light is emitted, the light transmitting and emitting light pipe sized to be extended through the sheath lumen to dispose the light pipe distal end in proximity with the vessel wall within the vessel lumen; and the surface probe element sensor comprises a photosensor that responds to the frequency of light emitted from the light pipe distal end and transmitted through the vessel wall and body tissue overlying the vessel wall.

51. The system of claim 39, further comprising a marker adapted to be applied to the body tissue overlying the vessel wall at the determined location to mark the determined location.

52. The system of claim 39, wherein the vessel surface probe further comprises a marker adapted to be applied to the body tissue overlying the vessel wall at the determined location to mark the determined location.

53. The system of claim 39, further comprising a marker containing marking ink adapted to be applied to the body tissue overlying the vessel wall at the determined location to dispense marking ink to mark the determined location.

54. The system of claim 39, wherein the vessel surface probe further comprises a marker containing marking ink adapted to be applied to the body tissue overlying the vessel wall at the determined location to dispense marking ink to mark the determined location.

55. A system for identifying an obstruction in and a course of a coronary artery vessel in a surgical field that is hidden from direct view by epicardial tissue overlying an vessel arterial wall of the coronary artery surrounding an vessel arterial lumen of the coronary artery comprising:

a vessel lumen probe having a lumen probe element at or near a vessel lumen probe distal end adapted to be introduced through an arterial system and into the arterial lumen of the coronary artery, wherein the lumen probe element is adapted to be positioned adjacent a luminal side of the arterial wall; and a vessel surface probe having a surface probe element sensor adapted to be applied and moved about over the epicardial tissue overlying the arterial wall, the surface probe element sensor adapted to provide a proximity indicating signal indicating the degree of proximity of the surface probe element sensor to the lumen probe element, wherein the course of the coronary artery is determinable as a function of the relative strength of the signal when the surface probe element sensor is moved over the epicardial tissue overlying the arterial wall relative to the lumen probe element positioned within the arterial lumen, and wherein an obstruction within the coronary artery vessel is determinable as a function of the relative strength of the signal when the lumen probe element is moved within the arterial lumen.

56. The system of claim 55, wherein the vessel lumen probe further comprises means for sweeping the lumen probe element around the arterial wall within the coronary artery while monitoring the indication of proximity.

57. The system of claim 55, further comprising a marker adapted to be applied to the tissue overlying the arterial wall at the determined location to mark the determined location.

* * * * *